United States Patent [19]

Suzuki et al.

[11] Patent Number: 5,270,316
[45] Date of Patent: Dec. 14, 1993

[54] CONDENSED PURINE DERIVATIVES

[75] Inventors: Fumio Suzuki, Mishima; Junichi Shimada, Shizuoka; Takeshi Kuroda, Shizuoka; Kazuhiro Kubo, Shizuoka, all of Japan; Akira Karasawa, Huntingdon Valley, Pa.; Tetsuji Ohno, Shizuoka; Kenji Ohmori, Mishima, both of Japan

[73] Assignee: Kyowa Hakko Kogyo Co., Ltd., Tokyo, Japan

[21] Appl. No.: 599,758

[22] Filed: Oct. 19, 1990

[30] Foreign Application Priority Data

Oct. 20, 1989 [JP] Japan ................... 1-273403

[51] Int. Cl.⁵ ............... A61K 31/52; C07D 487/14
[52] U.S. Cl. ................... 514/267; 544/251; 544/265; 544/273; 544/276
[58] Field of Search ............... 514/262, 267; 544/251

[56] References Cited

U.S. PATENT DOCUMENTS

| | | | |
|---|---|---|---|
| 4,298,734 | 11/1981 | Temple, Jr. ................. | 544/251 |
| 5,064,947 | 11/1991 | Peet et al. .................. | 536/26 |
| 5,086,176 | 4/1992 | Peet et al. .................. | 544/251 |

FOREIGN PATENT DOCUMENTS

| | | | |
|---|---|---|---|
| 0390111 | 10/1990 | European Pat. Off. ............ | 544/251 |
| 0417790 | 3/1991 | European Pat. Off. ............ | 544/251 |

OTHER PUBLICATIONS

Sepiol et al., Chemical Abstracts, vol. 86: 29222k (1987).
Ohsaki et al., Chemical Abstracts, vol. 106: 84536x (1987).
Habraken et al., Chemical Abstracts, vol. 112: 191473v May 21, 1990.
Temple et al. J. Med. Chem., vol. 23, No. 11, pp. 1188-1198 (1980).
Ienaga et al. Liebigs Ann. Chem., vol. 11, pp. 1972-1880 (1979).

*Primary Examiner*—Mukund J. Shah
*Assistant Examiner*—E. Bernhardt
*Attorney, Agent, or Firm*—Fitzpatrick, Cella, Harper & Scinto

[57] ABSTRACT

There are disclosed condensed purine derivatives represented by formula;

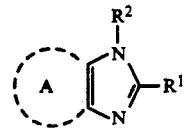

wherein 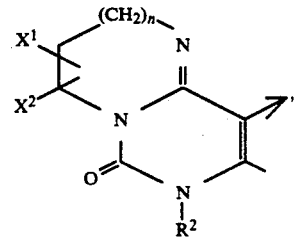 represents in which $R^3$ represents hydrogen, lower alkyl or benzyl; each of $X^1$ and $X^2$ independently represents hydrogen, lower alkyl, aralkyl or phenyl; and n is an integer of 0 or 1; $R^1$ represents hydrogen, lower alkyl, alicyclic alkyl, noradamantan-3-yl, dicyclopropylmethyl or styryl; and $R^2$ represents hydrogen, lower alkyl or alicyclic alkyl; or a pharmaceutically acceptable salt thereof. The derivatives and pharmaceutically acceptable salts are useful as diuretics, renal protecting agents, antiallergic agents and hypotensives.

8 Claims, No Drawings

CONDENSED PURINE DERIVATIVES

BACKGROUND OF THE INVENTION

The present invention relates to novel purine derivatives which possess diuretic, renal protecting, bronchodilatory, antiallergic and hypotensive effects.

As condensed purine derivatives which are structurally analogous to the presently claimed compounds, a compound represented by formula (A) and having a slight bronchodilatory effect is disclosed in J. Med. Chem., 23, 1188 (1980):

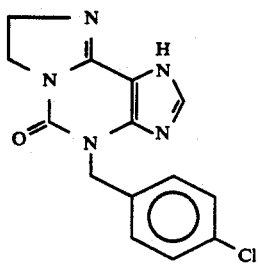
(A)

Compounds represented by formula (B) are disclosed in Liebigs. Ann. Chem., 11, 1872 (1979):

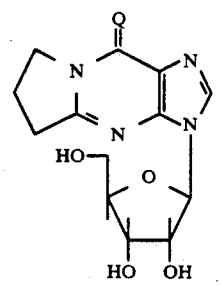
(B)

where Q is NH or O.

SUMMARY OF THE INVENTION

An object of the present invention is to provide novel condensed purine derivatives represented by the formula (I):

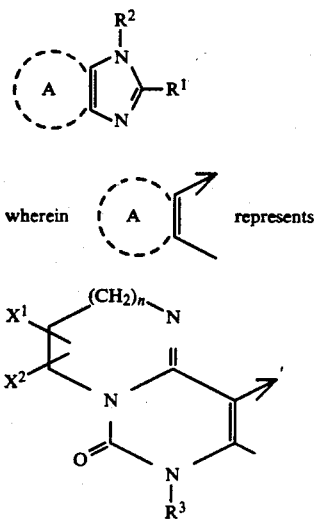
(I)

wherein 
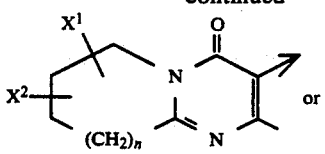 
represents 
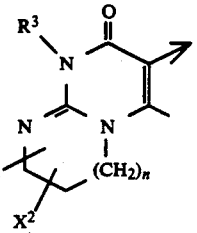
or in which $R^3$ represents hydrogen, lower alkyl or benzyl; each of $X^1$ and $X^2$ independently represents hydrogen, lower alkyl, aralkyl or phenyl; and n is an integer of 0 or 1; $R^1$ represents hydrogen, lower alkyl, alicyclic alkyl, noradamantan-3-yl, dicyclopropylmethyl or styryl; and $R^2$ represents hydrogen, lower alkyl, or alicyclic alkyl (hereinafter referred to as Compound (I), and other compounds with other formulae shall be likewise referred to); or a pharmaceutically acceptable salt thereof.

DETAILED DESCRIPTION OF THE INVENTION

In the definitions of the groups in formula (I), the lower alkyl refers to a straight or branched alkyl having 1 to 6 carbon atoms, and includes, for example, methyl, ethyl, propyl, isopropyl, butyl, isobutyl, sec-butyl, tert-butyl, pentyl, neopentyl, hexyl, etc. The alicyclic alkyl is those having 3 to 6 carbon atoms, and includes, for example, cyclopropyl, cyclopentyl, cyclohexyl, etc. The aralkyl is those having 7 to 15 carbon atoms, and includes, for example, benzyl, phenethyl, benzhydryl, etc.

The pharmaceutically acceptable salts of Compound (I) include acid addition salts, metal salts, ammonium salts, organic amine addition salts, amino acid addition salt, etc.

The pharmaceutically acceptable acid addition salts of Compound (I), include inorganic acid salt such as hydrochloride, sulfate, phosphate, etc. and organic acid salts such as acetate, maleate, fumarate, tartarate, citrate, etc. The pharmaceutically acceptable metal salts include alkali metal salts such as sodium salt, potassium salt etc.; alkaline earth metal salts such as magnesium salt, calcium salt, etc. and further an aluminum salt and a zinc salt. The pharmaceutically acceptable organic amine addition salts include addition salt of morpholine, piperidine, etc. The pharmaceutically acceptable amino acid addition salts include lysine, glycine, phenylalanine, etc.

The methods for preparing Compound (I) are described below.

When the defined groups are changed under the conditions of the following processes or are inadequate to proceeding of the following processes, processes can be readily carried out by a usual method in the organic synthetic chemistry, for example, by protection of functional groups, elimination of protecting groups.

PROCESS 1

Compound (Ia), which is a Compound (I) where

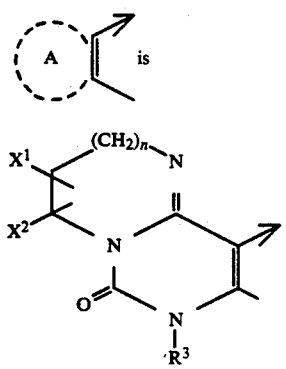

is synthesized according to the following reaction steps.

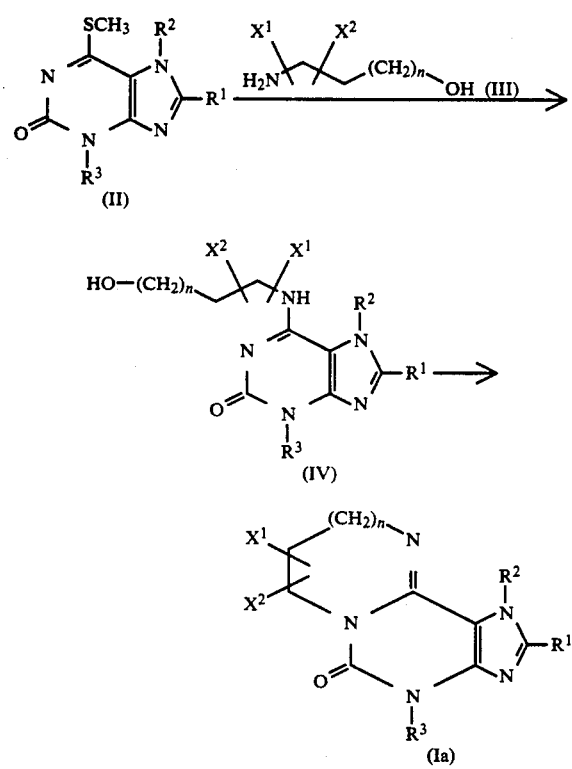

wherein $R^1$, $R^2$, $R^3$, $X^1$, $X^2$ and n have the same significance as described above Compound (IV) is obtained by reacting Compound (II) with Compound (III) in the absence or presence of a solvent. Any solvent is used so long as it is inert to the reaction. The solvent includes, for example, dimethylamines such as dimethylformamide, dimethylacetamide, etc.; kentones such as acetone, methyl ethyl ketone, etc.; aromatic hydrocarbons such as toluene, xylene, etc.; halogenated hydrocarbons such as dichloroethane, 1,1,2,2-tetrachloroethane, etc.; dimethylsulfoxide, etc. The solvent is used alone or in combination. The reaction is carried out at 50° to 80° C and completed in 5 minutes to 24 hours.

The starting Compound (II) is synthesized by a notorious method [J. Chem. Soc. Perkin I, 739 (1973)] or by a modified method of Perkin. The starting Compound (III) is commercially available.

Compound (Ia) is obtained by reacting Compound (IV) with a halogenating agent or an inorganic acid in the absence or presence of a solvent.

The halogenating agent includes, for example, thionyl chloride, phosphorus oxychloride, etc. The inorganic acid includes, for example, hydrochloric acid, hydrobromic acid, hydroiodic acid, phosphoric acid, etc.

The solvent includes, for example, halogenated hydrocarbons such as methylene chloride, chloroform, dichloroethane, etc.; dimethylformamide, dimethylsulfoxide, etc. The solvent is used alone or in combination. The reaction is carried out at $-10°$ to $150°$ C. and completed in 5 minutes to 24 hours.

PROCESS 2

Compound (Ib) which is Compound (I) where

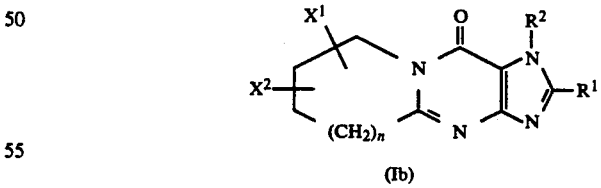

is synthesized according to the following reaction steps.

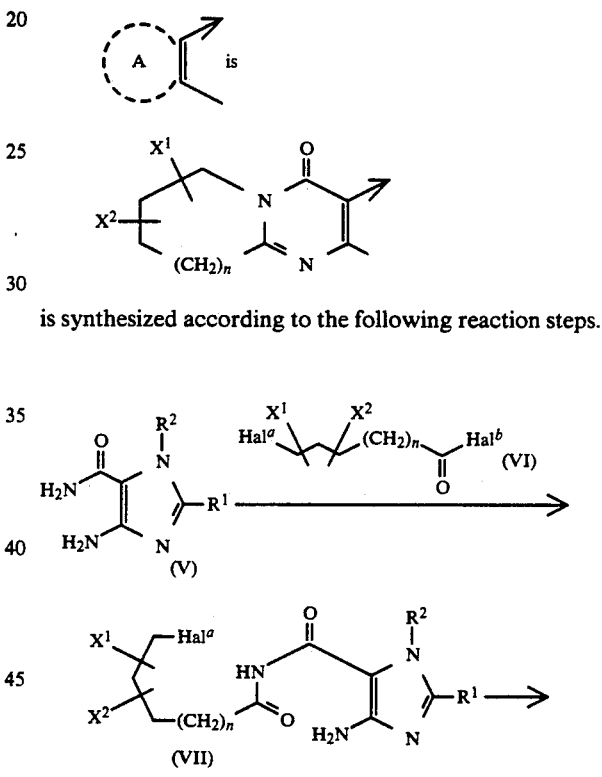

wherein each of $Hal^a$ and $Hal^b$ independently represents chlorine, bromine or iodine; and $R^1$, $R^2$, $X^1$, $X^2$ and n have the same significance as described above.

Compound (VII) is prepared by reacting Compound (V) with Compound (VI) in a solvent in the presence of a silyl compound. Examples of the silyl compound include bistrimethylsilylacetamide (BSA), bistrimethylsilyltrifluoroacetamide (BSTA), etc. Any solvent is used so long as it is inert to the reaction. The solvent includes, for example, ethers such as tetrahydrofuran, dioxane, etc.; alcohols such as methanol, ethanol, etc.;

dimethylformamide, dimethylsulfoxide, etc., and is used alone or in combination. The reaction is carried out at −78° to 150° C. and completed in 5 minutes to 24 hours.

Compound (Ib) is obtained by reacting Compound (VII) with an acid in the absence or presence of a solvent. Examples of the acid include an inorganic acid such as hydrochloric acid, sulfuric acid, phosphoric acid, etc.; or an organic acid such as methanesulfonic acid, acetic acid, etc. Any solvent can be used so long as it is inert to the reaction, and includes, for example, aromatic hydrocarbons such as benzene, toluene, etc.; alcohols such as methanol, ethanol, etc., dimethylformamide, etc. The solvent is used alone or in combination. The reaction is carried out by heating at 50° to 350° C. and completed in 5 minutes to 24 hours.

PROCESS 3

Compound (Ic) which is Compound (I) where

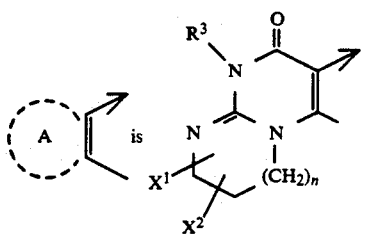

is synthesized according to the following reaction steps.

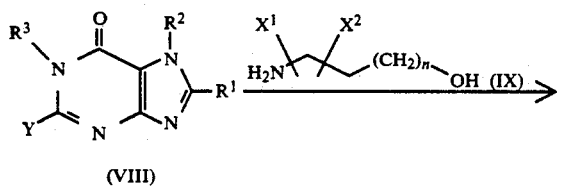

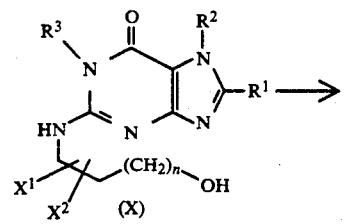

wherein Y represents a leaving group; and $R^1$, $R^2$, $R^3$, $X^1$, $X^2$ and n have the same significance as described above.

Examples of the leaving group denoted by Y include halogen such as chlorine, bromine, etc.; or methylthio, methanesulfonyloxy, etc.

Compound (X) is obtained by reacting Compound (VIII) with Compound (IX) in the absence or presence of a solvent. Any solvent is used so long as it is inert to the reaction.

The solvent includes, for example, ethers such as tetrahydrofuran, dioxane, etc.; amides such as dimethylformamide, etc.; alcohols such as methanol, ethanol, etc.; dimethylsulfoxide, etc., and is used alone or in combination. The reaction is carried out at 0° to 180° C. and completed in 30 minutes to 24 hours.

The starting Compound (VIII) is synthesized by a notorious method [Ber., 30, 2400 (1877)] or by its modified method.

Compound (Ic) is obtained by reacting Compound (X) with a halogenating agent or an inorganic acid.

The halogenating agent includes, for example, thionyl chloride, phosphorus oxychloride, etc. The inorganic acid includes, for example, hydrochloric acid, phosphoric acid, etc. The reaction is carried out at 0° to 180° C. and completed in 5 minutes to 24 hours.

PROCESS 4

Compound (I-1) is Compound (I) where $R^2$ represents groups other than hydrogen and Compound (I-2) obtained in Processes 1 through 3 is Compound (I) where $R^2$ represents hydrogen.

Compound (I-1) is obtained by reacting Compound (I-2) with Compound (XI) represented by the following formula in the presence or absence of a base.

wherein Z represents a leaving group and $R^{2a}$ has the same significance as that of $R^2$ except for hydrogen.

Examples of the leaving group denoted by Z include halogen such as chlorine, bromine, iodine, etc.; alkylsulfonyloxy such as methanesulfonyloxy, etc.; arylsulfonyloxy such as phenylsulfonyloxy, p-toluenesulfonyloxy, etc.

The base includes, for example, alkali metal carbonates such as potassium carbonate, sodium carbonate, etc.; hydrated alkali metals such as sodium hydride, etc.; alkali metal alkoxides such as sodium methoxide, sodium ethoxide, etc.

The solvent is used alone or in combination, and includes, for example, ethers such as tetrahydrofuran, dioxane, etc.; amides such as dimethylformamide, etc.; alcohols such as methanol, ethanol, etc.; dimethylsulfoxide and the like. The reaction is carried out at 0° to 180° C. and completed in 30 minutes to 24 hours.

PROCESS 5

Compound (Ic) can be prepared according to the following reaction steps.

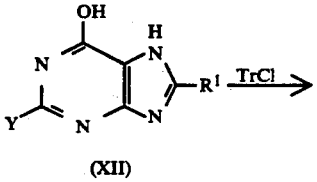

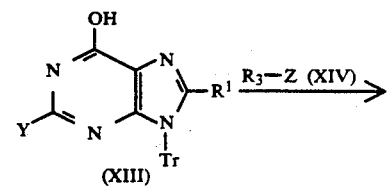

-continued

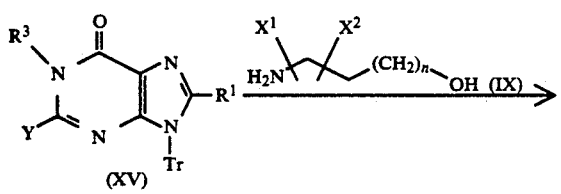

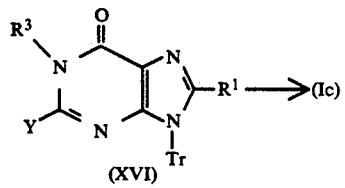

wherein Tr represents triphenylmethyl; and $R^1$, $R^3$, Y, Z, $X^1$, $X^2$ and n have the same significance as defined above.

Compound (XIII) is obtained by reacting Compound (XII) with TrCl, preferably in the presence of a base.

The solvent and base to be used in the reaction and the reaction condition are the same as mentioned in Process 4.

The starting Compound (XII) can be synthesized by a notorious method [J. Amer. Chem. Soc., 76, 5633 (1954)] or by its modified method.

Compound (XV) is obtained by reacting Compound (XIII) with Compound (XIV), preferably in the presence of a base.

The solvent and base to be used in the reaction and the reaction condition are the same as mentioned in Process 4.

Compound (XVI) is obtained by reacting Compound (XV) with Compound (IX) in the absence or presence of a solvent.

The solvent to be used in the reaction and the reaction condition are the same as mentioned in the step of Compound (VIII) to Compound (X) in Process 3.

Compound (Ic) is obtained by reacting Compound (XVI) with a halogenating agent or an inorganic acid.

The halogenating agent includes, for example, thionylchloride or phosphorus oxychloride, etc.

The inorganic acid includes, for example, hydrochloride or phosphoric acid, etc.

The reaction is performed at 0°~180° C. and completed in 5 minutes to 24 hours.

The intermediates and objective compounds in the respective methods described above can be isolated and purified by purification methods conventionally used in organic synthesis chemistry, for example, filtration, extraction, washing, drying, concentration, recrystallization, various column chromatographies, etc. Furthermore, the intermediates may also be provided in the subsequent reaction, without being further purified.

In the case that it is desired to obtain salts of Compound (I), when Compound (I) is obtained in the form of its salt, Compound (I) may be purified as it is. Further in the case that Compound (I) is obtained in the free form, its salts may be formed in a conventional manner, for example, Compound (I) is suspended or dissolved in an appropriate solvent, and an acid or base is added to the solution or suspension.

Furthermore, Compound (I) and pharmaceutically acceptable salts thereof may also be present in the form of addition products to water or to various solvents; in this case, the addition products are also included in the present invention.

Furthermore, some of Compounds (I) may have optical isomers. In the present invention, all possible stereoisomers and their mixtures are all included.

Specific examples of Compound (I) are shown in Tables 1-1 through 1-3.

TABLE I-1

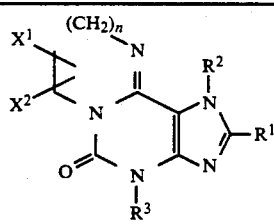

| Compound No. | $R^1$ | $R^2$ | $R^3$ | n | $X^1$ | $X^2$ |
|---|---|---|---|---|---|---|
| 1 | H | $CH_3$ | $(CH_2)_2CH_3$ | 0 | 8-H | 7-H |
| 2 | " | H | " | " | " | " |
| 3 | " | $CH_3$ | " | 1 | " | " |
| 4 | " | " | " | 0 | 8-$C_2H_5$ | " |
| 5 | " | " | " | " | 8-H | 7-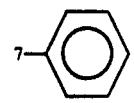 |
| 6 |  | H | " | " | " | 7-H |
| 7 | " | $CH_3$ | " | " | " | " |
| 8 | " | H | " | " | 8-$C_2H_5$ | |

TABLE I-1-continued
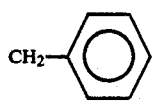
| Compound No. | R¹ | R² | R³ | n | X¹ | X² |
|---|---|---|---|---|---|---|
| 9 | H | " | 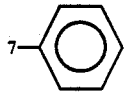 | " | 8-H | " |
| 10 | " | CH₃ | " | " | " | " |
| 11 | 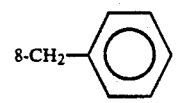 | H | (CH₂)₂CH₃ | " | " | 7- 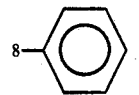 |
| 12 | " | " | " | " | 8-CH₂- 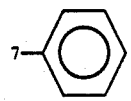 | 7-H |
| 13 | " | " | " | " | 8-CH(CH₃)₂ | " |
| 14 | " | " | " | " | 8-CH₃ | 8-CH₃ |
| 15 | " | " | " | " | 8-  | 7-H |
| 16 | " | " | " | " | 8-CH₃ | " |
| 17 | " | " | " | " | 8-(CH₂)₂CH₃ | " |
| 18 | " | " | " | " | 8-H | 7-C₂H₅ |
| 19 | " | " | " | " | " | 7-CH₃ |
| 20 |  | " | " | " | 8-C₂H₅ | 7-H |
| 21 |  | " | " | " | " | " |
| 22 |  | CH₃ | " | " | " | " |
| 23 | H | H | " | " | 8-H | 7-  |

TABLE I-2

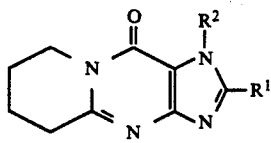

| Compound No. | R² | R¹ |
|---|---|---|
| 24 | H | H |
| 25 | CH₃ | H |
| 26 | (CH₂)₃CH₃ | H |
| 30 | H | (1-adamantyl) |
| 31 | H | (dicyclopropylmethyl) |
| 32 | H | (styryl/phenylvinyl) |

TABLE I-3

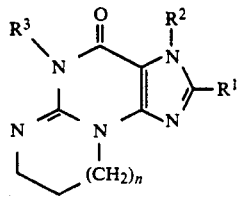

| Compound No. | R¹ | R² | R³ | n |
|---|---|---|---|---|
| 27 | H | CH₃ | (CH₂)₃CH₃ | 0 |
| 28 | " | " | " | 1 |
| 29 | " | H | CH₃ | 0 |
| 33 | (1-adamantyl) | CH₃ | (CH₂)₃CH₃ | " |
| 34 | (dicyclopropylmethyl) | " | " | " |
| 35 | (styryl) | " | " | " |
| 36 | (1-adamantyl) | " | " | 1 |

TABLE I-3-continued

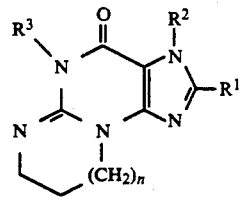

| Compound No. | R¹ | R² | R³ | n |
|---|---|---|---|---|
| 37 | (dicyclopropylmethyl) | " | " | " |
| 38 | (styryl) | " | " | " |
| 39 | (1-adamantyl) | H | CH₃ | 0 |
| 40 | (dicyclopropylmethyl) | " | " | " |
| 41 | (styryl) | " | " | " |

Compound (I) or its pharmaceutically acceptable salts have diuretic, renal protecting, bronchodilatory and hypotensive activities, etc. Accordingly, Compound (I) or its pharmaceutically acceptable salts are useful as diuretics, renal protecting agents, bronchodilatory agents, antiallergic agents and hypotensives.

Next, pharmaceutical activities of Compound (I) are explained below.

(1) Acute Toxicity

The compounds were orally administered to male dd-mice weighing 20±1 g. Minimum lethal dose (MLD) was determined by observing the mortality for seven days after the administration.

The results are shown in Table 2.

TABLE 2

| Compound | MLD (mg/kg) |
|---|---|
| 1 | >300 |
| 4 | >300 |
| 5 | >300 |
| 9 Sa | >300 |
| 10 Sa | >300 |
| 11 Sa | >300 |
| 12 Sa | >300 |
| 14 Sa | >300 |
| 15 Sa | >300 |

TABLE 2-continued

| Compound | MLD (mg/kg) |
|---|---|
| 17 Sa | >300 |
| 18 Sa | >300 |
| 19 Sa | >300 |
| 24 | >300 |
| 25 | >300 |

*Sa is hydrochloride of the Compound.

(2) Diuretic Activity

Wistar male rats weighing 150 to 300 g were used after they were fasted for 18 hours. A test compound or saline (control) was orally administered to rats and urine was collected for 6 hours. The test was performed using 3 groups per the test compound, and each group consists of 3 animals. The urine was metered by a measuring cylinder and electrolytes ($Na^+$ and $K^+$) in the urine were assayed with a flame photometer (model 775A manufactured by Hitachi Ltd.).

The results are shown in Table 3.

Parameters in Table 3 are all expressed by relative value for control.

TABLE 3

| Compound | Dose (mg/kg) | Urine volume (%) | Excretion of $Na^+$ (%) | Excretion of $K^+$ (%) | $Na^+/K^+$ |
|---|---|---|---|---|---|
| Control | — | 0 | 0 | 0 | 1.00 |
| 5 | 25 | 165 | 197 | 77 | 1.67 |
| 6 | 1.6 | 121 | 102 | 30 | 1.55 |
| 7 | 25 | 128 | 114 | 56 | 1.37 |
| 8 | 6.25 | 42 | 46 | 1 | 1.45 |
| 9 Sa | 25 | 88 | 65 | 31 | 1.26 |
| 12 Sa | 1.6 | 159 | 102 | 33 | 1.52 |
| 13 Sa | 6.25 | 140 | 92 | 18 | 1.63 |
| 14 Sa | 6.25 | 113 | 75 | 43 | 1.23 |
|  | 25 | 145 | 162 | 31 | 2.00 |
| 15 Sa | 6.25 | 137 | 153 | 9 | 2.32 |
|  | 25 | 95 | 90 | 26 | 1.51 |
| 16 Sa | 1.6 | 80 | 99 | 31 | 1.52 |
| 17 Sa | 6.25 | 138 | 158 | 18 | 2.91 |
| 18 Sa | 25 | 92 | 65 | 37 | 1.20 |
| 19 Sa | 25 | 111 | 87 | 31 | 1.43 |
| Furosemide** | 25 | 75 | 64 | 57 | 1.07 |

*Sa is hydrochloride of the Compound
**The Merck Index 11th ed., 4221 (1989)

(3) Effect on Renal Protecting Activity
(Glycerol-induced Renal Deficient Model)

Renal insufficiency is the condition that homeostasis of body fluid failed to maintain by disorder of renal function. It is well known that subcutaneous or intramuscular administration of glycerol to rat induce acute renal insufficiency characterized by renal tubular disturbance [Can J. Physiol. Pharmacol., 65, 42 (1987)].

Wistar male rats (fasted both food and water for 18 hours) were used. A test compound or saline (control) was intraperitoneally administered (dose: 10 mg/kg) to rats. After 30 minutes rats were anesthesized with ether and the back skin was picked up and 0.8 ml/100 g of 50% glycerol was subcutaneously administered. 24 hours after the glycerol injection, the rats were anesthesized with ether and 5 ml of the blood was collected from the descending aorta. To obtain the serum, after allowing it to stand for 30 minutes or longer, the blood sample was centrifuged at 3000 rpm for 10 minutes. Creatinine in the serum sample was determined using autoanalyzer (AU510, Olympus) or clinical analysis kit of creatinine (Creatinine Test Wako; by Wako Pure Chemical Ind., Japan). Urea nitrogen in the serum was determined using autoanalyzer (AU510; made by Olympus Optical Co., Ltd, Japan) or clinical analysis kit of urea nitrogen (Urea nitrogen test wako; by Wako Pure Chemical Ind., Japan).

The results are shown in Table 4.

Further, the left kidneys of test compound-treated groups and control groups were taken out from the animals and the kidneys were prepared for pathological sample.

As the result of pathologic autopsy for kidneys, it was indicated that the renal insufficiency was improved by the test compounds as shown in Table 4.

TABLE 4

| | Creatinine in serum (mg/dl) Glycerol treated | | Urea nitrogen in serum (mg/dl) Glycerol treated | |
|---|---|---|---|---|
| Compound No. | Control | Test compound administrated (Significance for control*) | Control | Test compound administrated (Significance for control*) |
| 1 | 2.64 ± 0.27 | 1.94 ± 0.16 P < 0.005 | | |
| 2 | 2.49 ± 0.43 | 1.63 ± 0.19 P < 0.1 | | |
| 6 | 5.01 ± 0.19 | 1.81 ± 0.12 P < 0.001 | | |
| 7 | 3.63 ± 0.29 | 1.70 ± 0.17 P < 0.001 | 137.9 ± 8.5 | 64.3 ± 7.1 P < 0.001 |
| 8 | 4.64 ± 0.24 | 3.17 ± 0.32 P < 0.01 | 147.0 ± 5.8 | 121.2 ± 9.0 P < 0.05 |
| 14 Sa | 4.81 ± 0.09 | 2.62 ± 0.40 P < 0.01 | 168.5 ± 3.5 | 94.8 ± 14.3 P < 0.01 |
| 15 Sa | 4.81 ± 0.09 | 2.34 ± 0.12 P < 0.001 | 168.5 ± 3.5 | 101.8 ± 11.8 P < 0.01 |
| 16 Sa | 4.81 ± 0.09 | 2.38 ± 0.24 P < 0.001 | 168.5 ± 3.5 | 80.9 ± 9.5 P < 0.001 |
| 17 Sa | 4.31 ± 0.12 | 2.35 ± 0.11 P < 0.001 | 147.1 ± 4.4 | 88.0 ± 4.9 P < 0.001 |
| 18 Sa | 4.31 ± 0.12 | 2.85 ± 0.33 P < 0.01 | 147.1 ± 4.4 | 101.2 ± 9.9 P < 0.01 |
| Aminophylline** | 2.03 ± 0.18 | 1.72 ± 0.07 N.S. | 46.2 ± 6.5 | 30.6 ± 2.0 P < 0.05 |
| Furocemide*** | 3.22 ± 0.35 | 4.17 ± 0.41 N.S. | 110.7 ± 9.4 | 150.3 ± 13.7 P < 0.05 |
| Normal control | Glycerol untreated 0.50 ± 0.02 | | Glycerol untreated 15.2 ± 0.9 | |

*Student-t test was used for level of significance
**The Merck Index 11th 477 (1989)
***The Merck Index 11th 4221 (1989)
N.S. No significant difference
Sa is hydrochloride of the compound.

(4) Effects on Passive Schultz-Dale Reaction
(Bronchodilatory Effects)

Guinea pigs were passively sensitized as follows. Hartley male guinea pigs weighing 350 to 500 g were injected intraperitoneally with rabbit anti-egg albumin (EWA) serum prepared by the method of Koda et al. [Folia pharmacol., Japon 66, 237, (1970)]. After 24 hours, the guinea pigs were stunned and exsanguinated, and then trachea was excised. The zig-zag strips of the trachea were prepared by the method of Emmerson and Mackay [J. Pharm. Pharmacol., 31, 798, (1979)]. The strips were suspended in Krebs-Henseleit solution at 37° C. under aeration of a mixed gas of 95% oxygen and 5% carbon dioxide, and incubated for one hour. Antigen (EWA) was then introduced in the solution (final concentration; 1 µg/ml), and the contraction was measured by isotonictrasducer (TD-112s, made by Nihon Kohden K.K., Japan) and recorded on a recorder (Type 3066, made by Yokogawa-Hokushin Denki, K.K. Japan).

After the contraction curves reached plateau the compounds were successively added in order to get cumulative concentration-relaxation curves. Concentration of 50% relaxation rate (IC50) was calculated from the regression line, which was obtained from cumulative concentration-relaxation curves.

The results are shown in Table 5.

(5) Inhibition Effect on Platelet Activating Factor (PAF)-induced Mortality

The experiment was performed by a minor modification of method of Carlson et al. [Agents and Actions, 21, 379 (1987)]. Groups each consisting of 10 male dd mice (weighing 28 to 32 g) were used, and 100 mg/kg of test compound or a saline (control) was orally administrated. One hour after the administration of test compound, 40 μg/kg of PAF (manufactured by Avanti Polar Lipids Co., Ltd.) was intravenously administered. Two hours after PAF injection, the mortality rate of the animals was observed. The compound whose mortality rate was significantly ($p<0.05$: Fischer's accurate probability tests) lower than control is regarded as having inhibitory effect on PAF-induced mortality, and the results in Table 5 were represented by minimum effective dose (MED).

TABLE 5

| Compound No. | Passive S - D reaction IC$_{50}$ (μM) | PAF-induced mortality inhibition MED (mg/kg) |
| --- | --- | --- |
| 1 | 0.0030 | >100 |
| 2 | 21 | 100 |
| 4 | 0.036 | >100 |
| 5 | 32 | NT*[3] |
| 6 | >40 | 50 |
| 7 | 8.1 | >100 |
| 8 | 72 | NT*[3] |
| 9 | >40 | 100 |
| 10 Sa | 9.7 | NT*[3] |
| 14 Sa | 11 | 100 |
| 15 Sa | >40 | 100 |
| Theophylline*[2] | 23 | 100 |

*[2]The Merck Index 11th ed., 9212 (1989)
*[3]not determined
Sa is hydrochloride of the compound.

(6) Effects on Experimental Asthma

Guinea pigs were passively sensitized as follows. Hartley male guinea pigs weighing 350 to 500 g were intraperitoneally injected with 1 ml of rabbit anti-egg alubmin (EWA) serum prepared by the method of Koda et al. [Folia pharmacol., Japon, 66, 237 (1970)]. The animals were treated with intraperitoneal injection of diphenhydramine (20 mg/kg) and propranolol (5 mg/kg), 30 minutes before administration of test compounds. 17 hours after the sensitization, the test compounds (50 mg/kg) or saline (control) were orally administered to sensitized animals. After one hour from the administration of the test compounds, the guinea pigs were placed in plastic observation box and were exposed to an aerosal antigen of 1.5% EWA.

The time until the onset of respiratory distress-like symptom [collapse time (second)] was measured as a result of experimental asthma.

The results are shown in Table 6.

TABLE 6

| Compound | Experimental asthma Collapse time (sec) |
| --- | --- |
| 2 | 552 ± 20 |
| 5 | 542 ± 36 |
| 10 Sa | 357 ± 65 |
| 13 Sa | 374 ± 76 |
| Theophylline* | 414 ± 47 |
| Control | 254 ± 18 |

*The Merck Index 11th ed., 9212 (1989)
Sa is hydrochloride of the compound.

Compounds (I) or their pharmaceutically acceptable salts are used directly or in various dosage forms. In the present invention, pharmaceutical compositions are prepared by homogeneously mixing an effective amount of Compound (I) or its pharmaceutically acceptable salt with pharmaceutically acceptable carrier. It is desirable that the pharmaceutical compositions are an appropriative dosable unit for oral administration or injection administration.

In the preparation of orally administrated forms, any of useful pharmaceutically acceptable carriers are used. In the case of orally administrated liquid preparates such as suspensions and syrups, for example, water, saccharides such as sucrose, sorbitol, fructose, etc., glycols such as polyethyleneglycol, propyleneglycol, etc., oils such as sesame oil, olive oil, soybean oil, etc., antiseptics such as p-hydroxybenzoic acid esters, etc., and flavors such as strawberry flavor, peppermint etc. are used. In the case of powder, pills, capsules and tablets; vehicles such as lactose, glucose, sucrose, mannitol, etc.; disintegrators such as starch, sodium alginate, etc.; lubricants such as magnesium stearate, talc, etc.; binders such as polyvinyl alcohol, hydroxypropyl cellulose, gelatin, etc., surfactants such as fatty acid esters etc., and plasticizers such as glycerine, etc., are used. Tablets and capsules are most useful dosage form for oral administration because of easy administration. In the preparation of tablets and capsules, solid medicament carriers are used.

Injection solutions are prepared with such a carrier as distilled water, a salt solution, a glucose solution, or a mixture of a salt solution and a glucose solution.

Effective dose and the number of administration of Compound (I) or its pharmaceutically acceptable salt depend on modes of administration and ages, body weight, and symptoms, etc. of patients. It is preferable to usually administer 1 to 50 mg/kg of Compound (I) or its pharmaceutically acceptable salt daily in 3 to 4 portions.

Furthermore, Compound (I) is administrated by inhalation in the form of aerosol, finely pulverized powders, or spray solution. In the case of aerosol administration, the present compound are dissolved in a pharmaceutically acceptable solvent, for example, ethyl alcohol or a combination of miscible solvents and then mixed with a pharmaceutically acceptable propellant.

Hereafter the present invention is described by referring to examples of the present invention and reference examples.

EXAMPLE 1

1-Methyl-4-n-propyl-1,4,7,8-tetrahydro-5H-imidazo[2,1-i]purin-5-one (Compound 1)

After 50 ml of ethanolamine was added to 5.00 g of Compound a obtained in Reference Example 1, the mixture was heated at 160° C. for an hour. After cooling, the reaction mixture was concentrated to the half in volume under reduced pressure. Ethanol was added to the concentrate and the precipitate was collected by filtration. Recrystallization from ethanol gave 3.52 g (67%) of 3,7-dihydro-6-(2-hydroxyethylamino)-7-methyl-3-n-propyl-2H-purin-2-one (Compound m1) as white plates.

Elemental analysis: as $C_{11}H_{17}N_5O_2$ Found (%): C 52.41 H 6.80 N 27.54. Calcd. (%): C 52.58 H 6.82 N 27.87.

$^1$H-NMR (DMSO-$d_6$, 90 MHz) δ (ppm): 6.82(brs, 1H), 4.87 (brs, 1H), 3.92(s, 3H), 3.91(t, 2H), 3.63–3.40 (m, 4H), 1.80–1.45(m, 2H), 0.88(t, 3H).

After 15 ml of phosphorus oxychloride was added to 3.50 g (13.9 mmol) of Compound m1 under ice cooling, the mixture was refluxed for 2 hours. Then the mixture was concentrated under reduced pressure. After neutralizing with 2N aqueous sodium hydroxide solution, the mixture was extracted 3 times with chloroform. After washing with saturated sodium chloride aqueous solution, the extract was dried over anhydrous sodium sulfate. The solvent was evaporated under reduced pressure. The residue was isolated and purified by silica gel column chromatography (eluting solvent: 2% methanol/chloroform) and then recrystallized from toluene to afford 1.27 g (39%) of Compound 1 as white needles.

Melting point: 109.9°–111.6° C. (toluene).

Elemental analysis: as $C_{11}H_{15}N_5O$ Found (%): C 56.49 H 6.57 N 30.23. Calcd. (%): C 56.64 H 6.48 N 30.02.

IR (KBr) νmax (cm$^{-1}$): 1685, 1657.

$^1$H-NMR (CDCl$_3$) δ (ppm): 7.43(s, 1H), 4.15–4.05(m, 2H), 3.95(s, 3H), 4.05–3.90(m, 4H), 1.90–1.70(m, 2H), 0.97(t, 3H).

EXAMPLE 2

4-n-Propyl-1,4,7,8-tetrahydro-5H-imidazo[2,1-i]purin-5-one (Compound 2)

The procedure was performed in a manner similar to Example 1 except for using 4 g (17.9 mmol) of Compound b obtained in Reference Example 2. Thus, 3.24 g (77%) of 3,7-dihydro-6-(2-hydroxyethylamino)-3-n-propyl-2H-purin-2-one (Compound m2) was obtained as a white powder.

$^1$H-NMR (DMSO-$d_6$, 90 MHz) δ (ppm): 7.82(s, 1H), 7.50 (brs, 1H), 3.88(t, 2H), 3.80–3.00(m, 5H), 1.90–1.40(m, 2H), 0.86(t, 3H).

Using 3.50 g (14.8 mmol) of the Compound m2, cyclization with phosphorus oxychloride was performed in a manner similar to Example 1 to afford 2.05 g (63%) of Compound 2 as a white powder.

Melting point: 282.8°–284.9° C. (water).

Elemental analysis: as $C_{10}H_{13}N_5O$ Found (%): C 54.54 H 6.05 N 32.15. Calcd. (%): C 54.78 H 5.98 N 31.94.

IR (KBr) νmax (cm$^{-1}$): 1718, 1660, 1550

$^1$H-NMR (DMSO-$d_6$-DCl) δ (ppm): 7.70(s, 1H), 4.12–3.85 (m, 6H), 1.80–1.60(m, 2H), 0.88(t, 3H)

$^{13}$C-NMR (DMSO-$d_6$) δ (ppm): 151.0, 149.1, 146.7, 143.9, 100.3, 45.3, 45.2, 20.6, 10.7.

EXAMPLE 3

1,4,5,7,8,9-Hexahydro-1-methyl-4-n-propyl-pyrimido[2,1-i]purin-5-one (Compound 3)

The procedure was performed in a manner similar to Example 1 except for using 2.45 g (10.3 mmol) of Compound a obtained in Reference Example 1 and 10 ml of propanolamine. Thus, 2.39 g (88%) of 3,7-dihydro-6-(3-hydroxypropylamino)-7-methyl-3-n-propyl-2H-purin-2-one (Compound m3) was obtained as a white powder $^1$H-NMR (DMSO-$d_6$, 90 MHz) δ (ppm): 7.79(s, 1H), 7.15–6.85(br, 1H), 4.50–4.10(br, 1H), 3.87(s, 3H), 3.86(t, 2H), 3.65–3.30(m, 4H), 1.90–1.40(m, 4H), 0.83(t, 3H).

After 20 ml of thionyl chloride was added to 1.84 g (6.94 mmol) of Compound m3, the mixture was stirred for 20 minutes. After concentration under reduced pressure, the reaction mixture was neutralized with 2N aqueous sodium hydroxide solution under ice cooling followed by extraction 3 times with chloroform. After washing with aqueous saturated sodium chloride solution, the extract was dried over anhydrous magnesium sulfate. The solvent was evaporated under reduced pressure. The residue was purified by silica gel column chromatography (eluting solvent: 5% methanol/chloroform) to afford 1.72 g (quantitative) of Compound 3 as white needles.

Melting point: 107.1°–108.6° C.

IR (KBr) νmax (cm$^{-1}$) 1679, 1643, 1542, 1484

$^1$H-NMR (CDCl$_3$) δ (ppm): 7.33(s, 1H), 3.98(s, 3H), 4.00–3.86(m, 4H), 3.54(t, 2H), 2.05–1.90(m, 2H), 1.85–1.65(m, 2H), 1.03–0.88(m, 6H).

$^{13}$H-NMR (CDCl$_3$) δ (ppm): 150.8, 144.5, 141.6, 139.4, 107.4, 44.6, 43.7, 42.1, 34.4, 21.5, 20.9, 11.2, MS (m/e) 247(M$^+$), 218, 204, 135.

EXAMPLE 4

8-Ethyl-1-methyl-4-n-propyl-1,4,7,8-tetrahydro-5H-imidazo[2,1-i]purin-5-one (Compound 4)

Using 4.00 g (16.8 mmol) of Compound a obtained in Reference Example 1 and 10 ml of 2-amino-1-butanol, the procedure was performed in a manner similar to Example 1 to afford 3.34 g (71%) of 3,7-dihydro-6-(1-ethyl-2-hydroxyethylamino)-7-methyl-3-n-propyl-2H-purin-2-one (Compound m4) as a white powder.

$^1$H-NMR (CDCl$_3$) δ (ppm): 7.42(s, 1H), 6.30–5.70(br, 1H), 4.40–3.50(m, 6H), 4.00(s, 3H), 1.95–1.40 (m, 4H), 1.05–0.70(m, 6H).

Using 3.20 g (11.5 mmol) of the compound m4, cyclization with phosphorus oxychloride was performed in a manner similar to Example 1 to afford 2.06 g (69%) of Compound 4 as white needles.

Melting point: 123.8°–125.5° C. (cyclohexane).

Elemental analysis: as $C_{13}H_{19}N_5O \cdot 0.3H_2O$ Found (%): C 58.30 H 7.68 N 26.50. Calcd. (%): C 58.54 H 7.41 N 26.26.

IR (KBr) νmax (cm$^{-1}$): 1698, 1668, 1655

$^1$H-NMR (CDCl$_3$) δ (ppm): 7.43(s, 1H), 4.23–4.18(m, 1H), 4.05–3.91(m, 3H), 3.97(s, 3H), 3.64–3.53(m, 1H), 1.90–1.50(m, 4H), 1.08–0.93(m, 6H).

EXAMPLE 5

1-Methyl-7-phenyl-4-n-propyl-1,4,7,8-tetrahydro-5H-imidazo[2,1-i]purin-5-one (Compound 5)

After 2.00 g (8.20 mmol) of Compound a obtained in Reference Example 1 was dissolved in 5 ml of dimethylsulfoxide, 5.76 g (42 mmol) of 2-amino-1-phenylethanol was added to the solution. Then the mixture was heated at 150° C. for an hour with stirring. After cooling, 100 ml of water was added and the mixture was extracted 4 times with chloroform. After washing with saturated aqueous sodium chloride solution, the extract was dried over anhydrous sodium sulfate. The solvent was evaporated under reduced pressure. The residue was isolated and purified by silica gel column chromatography (eluting solvent: 10% methanol/chloroform) to afford 1.67 g (62%) of 3,7-dihydro-6-(2-hydroxy-2-phenyl)ethylamino-7-methyl-3-n-propyl-2H-purin-2-one (Compound m5) as a white powder.

$^1$H-NMR (DMSO-d$_6$-D$_2$O, 90 MHz) δ (ppm): 8.30(s, 1H), 7.60-7.20(m, 5H), 4.94(dd, 1H, J=5, 8Hz), 4.07 (s, 3H), 4.20-3.70(m, 7H), 1.90-1.45(m, 2H), 0.91(t, 3H).

In a manner similar to Example 3, 1.51 g (4.61 mmol) of the Compound m5 was subjected to cyclization with thionyl chloride to afford 1.44 g (95%) of Compound 5 as white needles.

Melting point: 152.2°-153.6° C. (toluene-cyclohexane).

Elemental analysis: as C$_{17}$H$_{19}$N$_5$O Found (%): C 66.29 H 6.19 N 22.72. Calcd. (%): C 66.00 H 6.19 N 22.64.

IR (KBr) νmax (cm$^{-1}$) 1693, 1651

$^1$H-NMR (CDCl$_3$) δ (ppm): 7.45(s, 1H), 7.40-7.20(m, 5H), 5.29(dd, 1H, J=5.3, 10.7Hz), 4.49(dd, 1H, J=10.7, 14.8Hz), 3.99(dd, 1H, J=5.3, 14.8Hz), 3.87(t, 2H), 1.80-1.60(m, 2H), 0.90(t, 3H).

EXAMPLE 6

2-Cyclopentyl-4-n-propyl-1,4,7,8-tetrahydro-5H-imidazo[2,1-i]purin-5-one (Compound 6)

The procedure was performed in a manner similar to Example 1 except for using 5.00 g (17.1 mmol) of Compound e obtained in Reference Example 5 to afford 4.81 g (89%) of 8-cyclopentyl-3,7-dihydro-6-(2-hydroxyethylamino)-3-n-propyl-2H-purin-2-one (Compound m6) as a white powder.

$^1$H-NMR (DMSO-d$_6$, 90 MHz) δ (ppm): 7.08(brs, 1H), 3.89 (t, 2H), 3.56(s, 3H), 4.00-3.00(m, 6H), 2.20-1.45 (m, 10H), 0.88(t, 3H).

In a manner similar to Example 3, 3.08 g (10.1 mmol) of the Compound m6 was subjected to cyclization with thionyl chloride to afford 3.00 g (quantitative) of Compound 6 as white crystals.

Melting point: 214.9°-216.1° C. (dioxane).

Elemental analysis: as C$_{15}$H$_{21}$N$_5$O.1.3H$_2$O Found (%): C 57.90 H 7.29 N 22.63. Calcd. (%): C 57.97 H 7.65 N 22.53.

IR (KBr) νmax (cm$^{-1}$) 1712, 1670, 1588

$^1$H-NMR (DMSO-d$_6$) δ (ppm): 4.28-4.16(m, 2H), 4.12-3.90 (m, 4H), 3.40-3.25(m, 1H), 2.20-2.00(m, 2H), 1.90-1.60(m, 8H), 0.90(t, 3H).

EXAMPLE 7

2-Cyclopentyl-1-methyl-4-n-propyl-1,4,7,8-tetrahydro-5H-imidazo[2,1-i]purin-5-one (Compound 7)

The procedure was performed in a manner similar to Example 1 except for using 1.30 g (4.25 mmol) of Compound f obtained in Reference Example 6. Thus, 1.26 g (93%) of 8-cyclopentyl-3,7-dihydro-6-(2-hydroxyethylamino)-7-methyl-3-n-propyl-2H-purin-2-one (Compound m7) was obtained as a white powder.

$^1$H-NMR (DMSO-d$_6$, 90MHz) δ (ppm): 3.93(s, 3H), 3.92(t, 2H), 3.70-3.10(m, 5H), 2.10-1.45(m, 10H), 0.88(t, 3H).

In a manner similar to Example 3, 1.10 g (3.44 mmol) of Compound m7 was subjected to cyclization with thionyl chloride to afford 583 mg (56%) of Compound 7 as a white needle.

Melting point: 245.5°-247.1° C. (propanol-water).

IR (KBr) νmax (cm$^{-1}$): 1712, 1686, 1662.

$^1$H-NMR (DMSO-d$_6$) δ (ppm): 3.95(s, 3H), 3.87(t, 2H), 3.85(s, 4H), 3.40-3.20(m, 1H), 2.10-1.95(m, 2H), 1.90-1.60(m, 8H), 0.86(t, 3H).

MS (m/e) relative intensity: 301(M+), 272, 260.

EXAMPLE 8

2-Cyclopentyl-8-ethyl-4-n-propyl-1,4,7,8-tetrahydro-5H-imidazo[2,1-i]purin-5-one (Compound 8)

The procedure was performed in a manner similar to Example 1 except for using 3.00 g (10.3 mmol) of Compound e obtained in Reference Example 5. Thus, 2.63 g (77%) of 8-cyclopentyl-3,7-dihydro-6-(1-ethyl-2-hydroxyethyl)amino-3-n-propyl-2H-purin-2-one (Compound m8) was obtained as a white powder.

$^1$H-NMR (CDCl$_3$, 90 MHz) δ (ppm): 7.60(brs, 1H), 4.12 (t, 2H), 4.30-3.00(m, 7H), 2.35-1.10(m, 12H), 0.97(t, 3H), 0.68(t, 3H).

In a manner similar to Example 3, 2.20 g (6.60 mmol) of the Compound m8 was subjected to cyclization. The crude product was dissolved in 10 ml of methanol. 1 ml of methanol solution saturated with hydrogen chloride was added under ice cooling. The mixture was concentrated under reduced pressure. The resulting light yellow powders were recrystallized from ethanol to afford 542 mg (26%) of the hydrochloride of Compound 8 as a light yellow needle.

Melting point: 208.8°-209.6° C.

Elemental analysis: as C$_{17}$H$_{25}$N$_5$O.HCl Found (%): C 58.22 H 7.63 N 19.74. Calcd. (%): C 58.03 H 7.45 N 19.90.

IR (KBr) νmax (cm$^{-1}$): 1717, 1687, 1588

$^1$H-NMR (DMSO-d$_6$) δ (ppm): 14.0-13.4(br, 1H), 11.2-10.7 (br, 1H), 4.40-4.25(m, 2H), 3.98(t, 2H), 3.90-3.80 (m, 1H), 3.45-3.30(m, 1H), 2.20-2.05(m, 2H), 1.90-1.60(m, 8H), 0.97(t, 3H), 0.90(t, 3H).

EXAMPLE 9

4-Benzyl-1,4,7,8-tetrahydro-5H-imidazo[2,1-i]purin-5-one (Compound 9)

The procedure was performed in a manner similar to Example 1 except for using 2.20 g (8.08 mmol) of Compound i obtained in Reference Example 8. Thus, 2.28 g (99%) of 3-benzyl-3,7-dihydro-6-(2-hydroxyethylamino)-2H-purin-2-one (Compound m9) was obtained as a light yellow powder.

$^1$H-NMR (DMSO-d$_6$, 90 MHz) δ (ppm): 7.80(s, 1H), 7.75-7.45(br, 1H), 7.40-7.00(m, 5H), 5.12(s, 2H), 3.70-3.45(m, 5H).

Using 2.04 g (7.15 mmol) of Compound m9, cyclization with phosphorus oxychloride was performed in a manner similar to Example 1 to afford 830 mg (44%) of the hydrochloride of Compound 9 as a light yellow powder.

Melting point: 300.8°-301.9° C. (decomposed).

IR (KBr) νmax (cm$^{-1}$) 1711, 1671.

$^1$H-NMR (DMSO-d$_6$) δ (ppm): 13.0-11.0(br, 1H), 8.35(s, 1H), 7.50-7.25(m, 5H), 5.23(s, 2H), 4.32-4.21 (m, 2H), 4.16-4.02(m, 2H).

MS (m/e) 267(M+), 91.

EXAMPLE 10

4-Benzyl-1-methyl-1,4,7,8-tetrahydro-5H-imidazo[2,1-i]purin-5-one (Compound 10)

The procedure was performed in a manner similar to Example 1 except for using 2.20 g (7.69 mmol) of Compound h obtained in Reference Example 8. Thus, 1.83 g (80%) of 3-benzyl-3,7-dihydro-6-(2-hydroxyethylamino)-7-methyl-2H-purin-2-one (Compound m10) was obtained as a white powder.

$^1$H-NMR (DMSO-d$_6$, 90 MHz) δ (ppm): 7.83(s, 1H), 7.30–7.05(m, 5H), 6.93(brs, 1H), 5.08(s, 2H), 5.05–4.60(br, 1H), 3.90(s, 3H), 3.80–3.30(m, 4H).

Using 1.86 g (6.22 mmol) of Compound m10, cyclization with thionyl chloride was performed in a manner similar to Example 3 to afford 1.15 g (55%) of the hydrochloride of Compound 10 as light yellow needles.

Melting point: 168.0°–170.0° C. (acetonitrile).

Elemental analysis as C$_{15}$H$_{15}$N$_5$O.HCl.H$_2$O Found (%): C 53.63 H 5.52 N 20.84. Calcd. (%): C 53.65 H 5.40 N 20.86.

IR (KBr) νmax (cm$^{-1}$) 1709, 1678, 1593.

$^1$H-NMR (DMSO-d$_6$) δ (ppm): 11.8–11.4(br, 1H), 8.39(s, 1H), 7.45–7.20(m, 5H), 5.21(s, 2H), 4.30–4.18(m, 2H), 4.10–3.98(m, 2H), 4.02(s, 3H).

The same procedures as in Example 5 were performed in Examples 11 to 19 except that amino alcohols shown in Table 7 and 3.00 g (10.3 mmol) of Compound e obtained in Reference Example 5 were used.

The physicochemical data of Compounds 11 to 19 were given in Table 8.

EXAMPLE 11
2-Cyclopentyl-7-phenyl-4-n-propyl-1,4,7,8-tetrahydro-5H-imidazo[2,1-i]purin-5-one (Compound 11)

EXAMPLE 12
8-Benzyl-2-cyclopentyl-4-n-propyl-1,4,7,8-tetrahydro-5H-imidazo[2,1-i]purin-5-one (Compound 12)

EXAMPLE 13
2-Cyclopentyl-8-isopropyl-4-n-propyl-1,4,7,8-tetrahydro-5H-imidazo[2,1-i]purin-5-one (Compound 13)

EXAMPLE 14
2-Cyclopentyl-8,8-dimethyl-4-n-propyl-1,4,7,8-tetrahydro-5H-imidazo[2,1-i]purin-5-one (Compound 14)

EXAMPLE 15
2-Cyclopentyl-8-phenyl-4-n-propyl-1,4,7,8-tetrahydro-5H-imidazo[2,1-i]purin-5-one (Compound 15)

EXAMPLE 16
2-Cyclopentyl-8-methyl-4-n-propyl-1,4,7,8-tetrahydro-5H-imidazo[2,1-i]purin-5-one (Compound 16)

EXAMPLE 17
2-Cyclopentyl-4,8-di-n-propyl-1,4,7,8-tetrahydro-5H-imidazo[2,1-i]purin-5-one (Compound 17)

EXAMPLE 18
2-Cyclopentyl-7-ethyl-4-n-propyl-1,4,7,8-tetrahydro-5H-imidazo[2,1-i]purin-5-one (Compound 18)

EXAMPLE 19
2-Cyclopentyl-7-methyl-4-n-propyl-1,4,7,8-tetrahydro-5H-imidazo[2,1-i]purin-5-one (Compound 19)

TABLE 7

| Example No. | Aminoalcohol | Yield (%) |
|---|---|---|
| 11 | 2-Amino-1-phenylethanol | 64 |
| 12 | 2-Benzyl-2-aminoethanol | 71 |
| 13 | 2-Amino-3-methylbutanol | 61 |
| 14 | 2-Amino-2-methyl-1-propanol | 42 |
| 15 | 2-Phenylglycinol | 49 |
| 16 | 2-Amino-1-propanol | 85 |
| 17 | 2-Amino-1-pentanol | 65 |
| 18 | 1-Amino-2-butanol | 86 |
| 19 | 1-Amino-2-propanol | 73 |

TABLE 8

| Compound No. | Properties | Melting point (°C.) (Recrystallization solvent) | Elemental analysis (%) (upper: found lower: calcd.) | | | IR (KBr) νmax (cm$^{-1}$) | MS (m/e) Relative intensity | $^1$H-NMR (measuring solvent) δ(ppm) |
|---|---|---|---|---|---|---|---|---|
| | | | | C | H | N | | | |
| 11 Sa | white powder | 240.8–265.2 (ethanol) | C$_{21}$H$_{25}$N$_5$O.HCl | | | 1714, 1681, 1589 | 363 (M$^+$, 100) | 15.0–12.0(brs, 1H), 7.50–7.30(m, 5H), 5.68 (dd, J=4.5, 10.5Hz, 1H), 4.52(t, J=10.5Hz, 1H), 4.15–3.95(m, 3H), 3.40–3.25 (m, 1H), 2.30–2.15(m, 2H), 2.05–1.65(m, 8H), 0.90(t, 3H) |
| | | | 63.38 | 6.82 | 17.57 | | | |
| | | | 63.07 | 6.55 | 17.51 | | | |
| 12 Sa | white powder | 215.2–220.8 (ethanol) | C$_{22}$H$_{27}$N$_5$O.HCl | | | 1722, 1682, 1591 | 377 (M$^+$, 4), 336 (6), 286 (100), 244 (18) | 12.00–10.00(brs, 1H), 7.40–7.20(m, 5H), 4.75–4.65 (m, 1H), 4.21(dd, J=9.5, 9.0Hz, 1H), 4.15–4.00 (m, 3H), 3.40–3.25(m, 1H), 3.23(dd, J=4.5, 14.0Hz, 1H), 3.00(dd, J=8.0, 14.0Hz, 1H), 2.30–2.15 (m, 2H), 2.00–1.65(m, 8H), 0.95(t, 3H) |
| | | | 63.68 | 7.14 | 16.82 | | | |
| | | | 63.83 | 6.82 | 16.92 | | | |
| 13 Sa | light brown powder | 109.0–112.5 (cyclohexane-toluene) | C$_{18}$H$_{27}$N$_5$O.½HCl.H$_2$O | | | 1717, 1681, 1593 | 329 (M$^+$, 8), 286 (100), 244 (18) | 11.32(brs, 1H), 4.40–4.00 (m, 6H), 3.40–3.20(m, 1H), 2.25–2.10(m, 4H), 2.00–1.60(m, 6H), 1.15–0.90(m, 9H) |
| | | | 59.11 | 8.29 | 18.81 | | | |
| | | | 59.12 | 8.13 | 19.15 | | | |
| 14 Sa | white powder | 221.8–231.8 (toluene-ethanol) | C$_{17}$H$_{25}$N$_5$O.HCl | | | 1722, 1683, 1591 | 315 (M$^+$, 20), 300 (100), 258 (18) | 4.11(t, 2H), 4.04(s, 2H), 3.35–3.20(m, 1H), 2.25–2.10 (m, 4H), 2.00–1.60(m, 8H), 1.62(s, 6H). 0.99(t, 3H) |
| | | | 58.13 | 7.78 | 19.81 | | | |
| | | | 58.03 | 7.45 | 19.90 | | | |
| 15 Sa | mud yellow powder | 215.2–219.0 (chloroform- | C$_{21}$H$_{25}$N$_5$O.HCl.0.2H$_2$O | | | 1726, 1690, 1594 | 363 (M$^+$, 100) | 7.45–7.25(m, 5H), 5.54 (dd, J=7.5, 10.5Hz, 1H), 4.72(dd, J=10.5, 11.5Hz), |
| | | | 62.61 | 6.99 | 16.93 | | | |

TABLE 8-continued

| Compound No. | Properties | Melting point (°C.) (Recrystallization solvent) | Elemental analysis (%) (upper: found lower: calcd.) | | | IR (KBr) vmax (cm$^{-1}$) | MS (m/e) Relative intensity | $^1$H-NMR (measuring solvent) δ(ppm) |
|---|---|---|---|---|---|---|---|---|
| | | ether) | 62.51 | 6.59 | 17.33 | | | 4.18(dd, J=7.5, 11.5Hz, 1H), 4.12(t, 2H), 3.35–3.20 (m, 1H), 2.25–2.10(m, 1H), 2.00–1.65(m, 8H), 1.00(t, 3H) |
| 16 Sa | light yellow needles | 186.3–192.2 (ethylacetate) | C$_{16}$H$_{23}$N$_5$O.HCl.0.2H$_2$O | | | 1712, 1670, 1587 | 301 (M$^+$, 31), 286 (100), 244 (27) | 4.60–4.50(m, 1H), 4.43 (dd, J=10.0, 11.0Hz, 1H), 4.11(t, 2H), 3.88(dd, J=7.0, 11.0Hz, 1H), 3.30–3.20 (m, 1H), 2.20(m, 2H), 1.95–1.65(m, 8H), 1.86(d, 3H), 0.99(t, 3H) |
| | | | C | H | N | | | |
| | | | 56.48 | 7.63 | 20.51 | | | |
| | | | 56.28 | 7.20 | 20.51 | | | |
| 17 Sa | white powder | 202.3–204.4 (ethylacetate) | C$_{18}$H$_{27}$N$_5$O.HCl | | | 1719, 1692, 1588 | 329 (m$^+$, 14), 286 (100), 244 (20) | 4.50–4.30(m, 2H), 4.10 (t, 2H), 3.95–3.85(m, 1H), 3.30–3.15(m, 1H), 2.20–2.05 (m, 2H), 1.95–1.40(m, 10H), 1.05–0.90(m, 6H) |
| | | | C | H | N | | | |
| | | | 59.17 | 7.88 | 19.48 | | | |
| | | | 59.08 | 7.71 | 19.14 | | | |
| 18 Sa | light yellow powder | 160.4–163.3 (isopropanol-ethylacetate) | C$_{17}$H$_{25}$N$_5$O.HCl.2H$_2$O | | | 1717, 1652 | 315 (M$^+$, 76), 286 (100), 244 (25) | 4.30–3.85(m, 5H), 3.30–3.15(m, 1H), 2.25–2.60(m, 10H), 1.14 (t, 3H), 1.00(t, 3H) |
| | | | C | H | N | | | |
| | | | 52.92 | 7.65 | 18.07 | | | |
| | | | 52.88 | 7.78 | 18.14 | | | |
| 19 Sa | white powder | 162.0–163.9 (ethylacetate) | C$_{16}$H$_{23}$N$_5$O.HCl.2H$_2$O | | | 1715, 1674 | 301 (M$^+$, 100) | 4.50–4.35(m, 1H), 4.16 (t, 2H), 4.10–3.80(m, 2H), 3.30–3.15(m, 1H), 2.20–2.05 (m, 1H), 2.00–1.60(m, 6H), 1.71(d, 3H), 1.00(t, 3H) |
| | | | C | H | N | | | |
| | | | 51.57 | 7.29 | 19.05 | | | |
| | | | 51.64 | 7.53 | 18.82 | | | |

Sa is hydrochloride of the compound.

EXAMPLE 20

8-Ethyl-2-(noradamantan-3-yl)-4-n-propyl-1,4,7,8-tetrahydro-5H-imidazo[2,1-i]purin-5-one (Compound 20)

The procedure was performed in a manner similar to Example 5 except for using 3.00 g (8.72 mmol) of Compound k obtained in Reference Example 10 and 4.14 ml (43.6 mmol) of 2-amino-1-butanol. Thus 3.00 g (yield, 89%) of 3,7-dihydro-6-(1-ethyl-2-hydroxyethylamino)-8-(noradamantan-3-yl)-3-n-propyl-2H-purin-2-one (Compound m20) was obtained as a light yellow powder.

$^1$H-NMR (CDCl$_3$, 90 MHz) δ (ppm): 4.00–3.70(m, 5H), 2.82(t, 1H), 2.30–1.35(m, 16H), 1.05–0.85(m, 6H).

Using 2.78 g (7.22 mmol) of Compound m20, cyclization with thionyl chloride was performed in a manner similar to Example 8 to afford 1.52 g (yield, 52%) of hydrochloride of Compound 20 as light yellow needles.

Melting point: 196.3°–201.3° C. (ethylacetate).

Elemental analysis: as C$_{21}$H$_{29}$N$_5$O.HCl.0.25H$_2$O Found (%): C 61.66 H 7.51 N 17.00. Calcd (%): C 61.75 H 7.53 N 17.15.

IR (KBr) vmax (cm$^{-1}$) 1714, 1681, 1594.

$^1$H-NMR (CDCl$_3$, 90 MHz) δ (ppm): 4.50–3.90(m, 5H), 2.70(t, 1H), 2.55–1.60(m, 16H), 1.10(t, 3H), 0.96(t, 3H).

EXAMPLE 21

2-(Dicyclopropylmethyl)-8-ethyl-4-n-propyl-1,4,7,8-tetrahydro-5H-imidazo[2,1-i]purin-5-one (Compound 21)

The procedure was performed in a manner similar to Example 5 except for using 2.60 g (8.17 mmol) of Compound l obtained in Reference Example 11 and 5 ml of 2-amino-1-butanol. Thus, 2.17 g (yield, 74%) of 8-(dicyclopropylmethyl)-3,7-dihydro-6-(1-ethyl-2-hydroxyethylamino)-3-n-propyl-2H-purin-2-one (Compound m21) was obtained as a light yellow powder.

$^1$H-NMR (DMSO-d$_6$, 90 MHz) δ (ppm): 12.2(brs, 1H), 7.20 (brs, 1H), 4.30–3.30(m, 6H), 2.00–0.10(m, 21H)

Using 2.03 g (5.65 mmol) of Compound m21, cyclization with thionyl chloride was performed in a manner similar to Example 8 to afford 1.66 g (yield, 86%) of hydrochloride of Compound 21 as a light yellow powder.

Melting point: 153.1°–157.2° C. (cyclohexane-toluene).

Elemental analysis: as C$_{19}$H$_2$ N$_5$O.HCl.½H$_2$O Found (%): C 59.62 H 7.46 N 18.40. Calcd (%) C 59.67 H 7.51 N 18.31.

IR (KBr) vmax (cm$^{-1}$): 1720, 1678, 1591

$^1$H-NMR (CDCl$_3$, 90 MHz) δ (ppm): 4.50–3.90(m, 3H), 4.05(t, 2H), 2.00–1.60(m, 5H), 1.25–0.25(m, 16H), MS (m/e, relative intensity): 341(M$^+$, 12), 312(100).

EXAMPLE 22

8-Ethyl-1-methyl-4-n-propyl-2-styryl-1,4,7,8-tetrahydro-5H-imidazo[2,1-i]purin-5-one (Compound 22)

The procedure was performed in a manner similar to Example 5 except for using 1.72 g (5.06 mmol) of Compound n obtained in Reference Example 13. Thus, 1.49 g (yield, 77%) of 3,7-dihydro-6-(1-ethyl-2-hydroxyethylamino)-7-methyl-3-n-propyl-8-styryl-2H-purin-2-one (Compound m22) was obtained as a light yellow powder.

$^1$H-NMR (CDCl$_3$, 90 MHz) δ (ppm): 7.70(d, J=15.0Hz, 1H), 7.65–7.15(m, 5H), 6.86(d, J=15.0Hz, 1H), 4.50–3.55(m, 5H), 3.97(s, 3H), 2.00–1.45(m, 4H), 1.15–0.80(m, 6H).

Using 1.30 g (3.41 mmol) of Compound m22, cyclization with thionyl chloride was performed in a manner similar to Example 8 to afford 530 mg (yield, 39%) of hydrochloride of Compound 22 as a white powder.

Melting point: 198.7°-203.4° C. (isopropanol).

IR (KBr) νmax (cm$^{-1}$): 1706, 1670.

$^1$H-NMR (DMSO-d$_6$, 90 MHz) δ (ppm): 8.05-7.75(m, 3H), 7.60-7.30(m, 4H), 4.45-3.80(m, 5H), 4.20(s, 3H), 2.00-1.60(m, 4H), 1.10-0.85(m, 6H).

MS (m/e, relative intensity): 363(M$^+$, 17), 334(100).

EXAMPLE 23

7-Phenyl-4-n-propyl-1,4,7,8-tetrahydro-5H-imidazo[2,1-i]purin-5-one (Compound 23)

The procedure was performed in a manner similar to Example 5 except for using 3.00 g (13.4 mmol) of Compound b obtained in Reference Example 2 and 9.10 g (67.0 mmol) of 2-amino-1-phenylethanol. Thus, 3.66 g (yield, 87%) of 3,7-dihydro-6-(2-hydroxy-2-phenyl)ethylamino-3-n-propyl-2H-purin-2-one (Compound m23) was obtained as a white powder.

$^1$H-NMR (DMSO-d$_6$, 90 MHz) δ (ppm): 7.87(s, 1H), 7.65-7.20(m, 5H), 5.80(brs, 1H), 4.80(dd, J=5.0, 9.0Hz, 1H), 4.00-3.50(m, 4H), 1.80-1.45(m, 2H), 0.89(t, 3H).

Using 3.47 g (11.1 mmol) of Compound m23, cyclization with thionyl chloride was performed in a manner similar to Example 8 to afford 1.95 g (yield, 60%) of Compound 23 as white needles.

Melting point: 258.2°-263.5° C. (ethanol).

Elemental analysis: as C$_{16}$H$_{17}$N$_5$O.HCl.0.1H$_2$O Found (%): C 57.47 H 5.38 N 21.19. Calcd. (%): C 57.61 H 5.50 N 20.99.

IR (KBr) νmax (cm$^{-1}$): 1709, 1670, 1588.

$^1$H-NMR (DMSO-d$_6$, 90 MHz) δ (ppm): 8.11(s, 1H), 7.43 (s, 5H), 5.80(dd, J=5, 10Hz, 1H), 4.53(dd, J=10, 10Hz, 1H), 4.15-3.80(m, 3H), 1.85-1.50(m, 2H), 0.88(t, 3H).

MS (m/e, relative intensity): 295(M$^+$, 100), 266(41), 253(20).

EXAMPLE 24

1,5,6,7,8,10-Hexahydropyrido[1,2-a]purin-10-one (Compound 24)

After 15.1 g (0.0933 mol) of 4-amino-5-carboxyamidoimidazole hydrochloride was suspended in 400 ml of tetrahydrofuran, 68 ml (0.279 mol) of bistrimethylsilylacetamide was dropwise added to the suspension. After 30 minutes, 18.8 g (0.121 mol) of 5-chlorovaleryl chloride was added to the mixture under ice cooling. After stirring at room temperature for one hour, the solvent was evaporated under reduced pressure. After adding 200 ml of water, the mixture was neutralized with 50% sodium hydroxide under ice cooling followed by extraction with ethyl acetate. The extract was washed with brine and dried over anhydrous sodium sulfate. Evaporation of the solvent under reduced pressure gave 23.5 g (100%) of 4-amino-5-(N-5'-chlorovaleryl)carboxyimidazole (Compound m24) as white crystals.

$^1$H-NMR (DMSO-d$_6$, 90 MHz) δ (ppm): 7.80(s, 1H), 3.70 (t, 2H, J=7Hz), 3.04(t, 2H, J=7Hz), 1.86-1.55 (m, 4H).

MS (m/e): 246(M$^+$), 244.

To 10 g of Compound m24 was added 60 g of polyphosphoric acid. The mixture was stirred at 150° C. for 30 minutes. The reaction mixture was ice-cooled and 100 g of ice was added. The mixture was neutralized with 50% aqueous sodium hydroxide solution. The precipitate was collected by filtration to afford 2.8 g (36%) of Compound 24 as white crystals.

Melting point: above 300° C. (dimethylformamide).

IR (KBr) νmax (cm$^{-1}$) 1635.

$^1$H-NMR (CDCl$_3$/CD$_3$OD=4/1) δ (ppm): 8.03(s, 1H), 4.36 (t, 2H, J=7Hz), 3.07(t, 2H, J=7Hz), 2.22-2.03(m, 4H), MS (m/e): 190(M$^+$).

High resolution power MS (m/e): Found: 190.0872. Calcd.: 190.0854 (C$_9$H$_{10}$N$_4$O).

EXAMPLE 25

1-Methyl-1,5,6,7,8,10-hexahydropyrido[1,2-a]purin-10-one (Compound 25)

After 1.20 g (6.32 mmol) of Compound 24 obtained in Example 24 was suspended in 20 ml of dimethylformamide, 0.265 g (6.63 mmol) of 60% sodium hydride was added to the suspension at 0° C. After 30 minutes, 0.433 ml (6.95 mmol) of iodomethane was added and the mixture was stirred at room temperature for 1.5 hours. The precipitate was collected by filtration and recrystallized from isopropanol–diisopropyl ether to afford 0.700 g (54.3%) of Compound 25 as colorless crystals.

Melting point: 158°-161° C. (decomposed).

IR (KBr) νmax (cm$^{-1}$) 1719, 1622, 1220.

$^1$H-NMR (DMSO-d$_6$) δ (ppm): 8.25(s, 1H), 4.18(t, 2H, J=7Hz), 3.98(s, 3H), 2.91(t, 2H, J=7Hz), 2.08-1.84(m, 4H)

MS (m/e): 204(M$^+$).

High resolution power MS (m/e): Found: 204.0989. Calcd. 204.1011 (C$_{10}$H$_{12}$N$_4$O).

EXAMPLE 26

1-n-Butyl-1,5,6,7,8,10-hexahydropyrido[1,2-a]purin-10-one (Compound 26)

After 1.20 g (6.32 mmol) of Compound 24 obtained in Example 24 was suspended in 20 ml of dimethylformamide, 0.265 g (6.63 mmol) of 60% sodium hydride was added to the suspension at 0° C. After 30 minutes, 0.755 ml (6.63 mmol) of iodobutane was added and the mixture was stirred at room temperature for 1.5 hours. The reaction mixture was filtered and the filtrate was concentrated under reduced pressure. The residue was purified by silica gel column chromatography (eluting solvent; chloroform:methanol=40:1) to afford 1.10 g (70.8%) of Compound 26 as white crystals.

Compound 26 was dissolved in 30 ml of ethyl acetate, and an excess of ethyl acetate saturated with hydrogen chloride was added to the solution. The precipitate was collected by filtration to afford the hydrochloride of Compound 26 as white crystals.

Melting point: 204°-216° C. (decomposed).

IR (KBr) νmax (cm$^{-1}$) 1719, 1618, 1227.

$^1$H-NMR (DMSO-d$_6$) δ (ppm): 4.39(t, 2H, J=7Hz), 4.27(t, 2H, J=7Hz), 3.07(t, 2H, J=7Hz), 2.10-1.73(m, 4H), 1.32-1.16(m, 4H), 0.89(t, 3H, J=7Hz).

MS (m/e): 246(M$^+$).

High resolution power MS (m/e): Found: 246.1461. Calcd.: 246.1480 (C$_{13}$H$_{18}$N$_4$O).

EXAMPLE 27

5-n-Butyl-3-methyl-3,5,7,8-tetrahydro-4H-imidazo[2,1-b]purin-4-one (Compound 27)

After 113 ml (1.87 mol) of ethanolamine was added to 9.00 g (0.0374 mol) of Compound j obtained in Reference Example 9, the mixture was stirred at an external temperature of 90° C. for 2.5 hours. The solvent was evaporated under reduced pressure. The residue was purified by silica gel column chromatography (eluting solvent; chloroform: methanol=15:1) to afford 5.25 g (53.0%) of 5-n-butyl-1,7-dihydro-2-(2'-hydroxyethyl-)amino-7-methyl-6H-purin-6-one (Compound m27) as an oily substance.

$^1$H-NMR (CDCl$_3$, 90 MHz) $\delta$ (ppm): 8.13(s, 1H), 3.99(s, 3H), 4.30–3.20(m, 8H), 1.91–1.10(m, 4H), 0.99(t, 3H, J=7Hz).

MS (m/e): 265(M+).

After 60 ml of thionyl chloride was added to 3.00 g (0.0113 mol) of Compound m27 the mixture was stirred at room temperature for one hour. The solvent was evaporated under reduced pressure. Under ice cooling, aqueous saturated sodium hydrogen carbonate solution was added, to the residue and the mixture was extracted with chloroform. The combined extracts were washed with brine, dried over anhydrous sodium sulfate and concentrated. The crude product was purified by silica gel column chromatography (eluting solvent: chloroform:methanol=30:1) to afford 2.30 g (82.0%) of Compound 27 as white crystals.

Melting point: 122°–124° C. (ethyl acetate).

IR (KBr) $\nu$max (cm$^{-1}$) 1695, 1384.

$^1$H-NMR (DMSO-d$_6$) $\delta$ (ppm): 7.90(s, 1H), 4.10(t, 2H, J=7Hz), 3.87(t, 2H, J=7Hz), 3.84(s, 3H), 3.87 (t, 2H, J=7Hz), 3.84(s, 3H), 3.83(t, 2H, J=7Hz), 1.62–1.50(m, 2H), 1.38–1.21(m, 2H), 0.90(t, 3H, J=7Hz).

MS (m/e): 247(M+).

High resolution power MS (m/e): Found: 247.1420. Calcd.: 247.1432 (C$_{12}$H$_{17}$N$_5$O).

EXAMPLE 28

5-n-Butyl-3-methyl-3,4,5,7,8,9-hexahydropyrimide[2,1-b]purin-4-one (Compound 28)

After 27.8 ml (0.374 mol) of propanolamine was added to 3.00 g (0.0124 mol) of Compound j obtained in Reference Example 9, the mixture was stirred at an external temperature of 100° C. for one hour. The solvent was evaporated under reduced pressure. The crude product was purified by silica gel column chromatography (eluting solvent; chloroform:methanol=15:1) to afford 3.36 g (96.5%) of 5-n-butyl-1,7-dihydro-2-(3'-hydroxypropyl)amino-7-methyl- 6H-purin-6-one (Compound m28).

$^1$H-NMR (CDCl$_3$, 90 MHz) $\delta$ (ppm): 8.15(s, 1H), 3.98(s, 3H), 4.41–3.15(m, 8H), 2.01–1.08(m, 6H), 1.00(t, 3H, J=7Hz).

MS (m/e): 279(M+).

After 60 ml of thionyl chloride was added to 3.00 g (0.0108 mol) of Compound m28, the mixture was stirred at room temperature for an hour. The solvent was evaporated under reduced pressure. Under ice cooling, aqueous saturated sodium hydrogencarbonate solution was added to the residue, and the mixture was extracted with chloroform. The combined extracts were washed with brine, dried over anhydrous sodium sulfate and concentrated. The crude product obtained was isolated and purified by silica gel column chromatography (eluting solvent: chloroform: methanol=50:1) to afford 1.55 g (55.0%) of free Compound 28 as an oily substance. Subsequently, the free compound was treated as in Example 26 to give the hydrochloride of Compound 28.

Melting point: 280°–286° C.

IR (KBr) $\nu$max (cm$^{-1}$) 1635.

MS (m/e): 261(M+).

High resolution power MS (m/e): Found: 261.1599. Calcd.: 261.1590 (C$_{13}$H$_{19}$N$_5$O).

EXAMPLE 29

5-Methyl-3,5,7,8-tetrahydro-4H-imidazo[2,1-b]purin-4-one (Compound 29)

4.49 g (8.74 mmol) of Compound p obtained in Reference Example 15 was added to the 25 ml (414 mmol) of ethanolamine and the mixture was stirred for 30 minutes at external temperature 165° C. Water was added to the mixture, and the mixture was extracted with chloroform. The extract was washed with saturated brine, and was dried over magnesium sulfate. After filtration, the solvent was concentrated. The crude product was purified by silica gel column chromatography (eluting solvent: chloroform: methanol=20:1) to afford 0.42 g of 1,2-(2'-hydroxyethyl)amino-1-methyl-9-trityl-1H-purine-6-one (Compound 29). Compound m29 was added to 8 ml of thionylchloride and the mixture was stirred for 30 minutes. The solvent was evaporated under reduced pressure and ethanol was added to the residue. Trituration of the mixture afforded 0.194 g (yield, 11.6%) of hydrochloride of Compound 29, as a white powder.

Melting point: 308°–310° C.

IR (KBr) $\nu$max (cm$^{-1}$) 1714, 1646, 1576.

$^1$H-NMR (DMSO-d$_6$) $\delta$ (ppm): 8.17(s, 1H), 4.43(dd, 2H, J$_1$=7Hz, J$_2$=5.5Hz), 4.00(dd, 2H, J$_1$=7Hz, J$_2$=5.5Hz), 3.41(s, 3H).

MS (m/e): 190(M+-2), 191(M+-1), 192(M+).

EXAMPLE 30

2-(Noradamantan-3-yl)-1,5,6,7,8,10-hexahydropyrido[1,2-a]purin-10-one (Compound 30)

Using 4-amino-5-carboxyamido-2-(noradamantan-3-yl)imidazole hydrochloride, Compound 30 is obtained in a manner similar to Example 24.

EXAMPLE 31

2-Dicyclopropylmethyl-1,5,6,7,8,10-hexahydropyrido[1,2-a]purin-10-one (Compound 31)

Using 4-amino-5-carboxyamido-2-dicyclopropylmethyl imidazolehydrochloride, Compound 31 is obtained in a manner similar to Example 24.

EXAMPLE 32

2-Styryl-1,5,6,7,8,10-hexahydropyrido[1,2-a]purin-10-one (Compound 32)

Using 4-amino-5-carboxyamido-2-styrylimidazolehydrochloride, Compound 32 is obtained in a manner similar to Example 24.

EXAMPLE 33

2-(Noradamantan-3-yl)-5-n-butyl-3-methyl-3,5,7,8-tetrahydro-4H-imidazo[2,1-b]purin-4-one (Compound 33)

Using 2-chloro-8-(noradamantan-3-yl)-1-n-butyl-7-methyl-1,7-dihydro-6H-purin-6-one obtained in Reference Example 16, Compound 33 is obtained in a similar manner to Example 27.

EXAMPLE 34

2-Dicyclopropylmethyl-5-n-butyl-3-methyl-3,5,7,8-tetrahydro-4H-imidazo[2,1-b]purin-4-one (Compound 34)

Using 2-chloro-8-dicyclopropylmethyl-1-n-butyl-7-methyl-1,7-dihydro-6H-purin-6-one obtained in Reference Example 18, Compound 34 is obtained in a manner similar to Example 27.

EXAMPLE 35

2-Styryl-5-n-butyl-3-methyl-3,5,7,8-tetrahydro-4H-imidazo[2,1-b]purin-4-one (Compound 35)

Using 2-chloro-8-styryl-1-n-butyl-7-methyl-1,7-dihydro-6H-purin-6-one obtained in Reference Example 18, Compound 35 is obtained in a manner similar to Example 27.

EXAMPLE 36

2-(Noradamantan-3-yl)-5-n-butyl-3-methyl-3,4,5,7,8,9-hexahydropyrimido[2,1-b]purin-4-one (Compound 36)

Using 2-chloro-8-(noradamantan-3-yl)-1-n-butyl-7-methyl-1,7-dihydro-6H-purin-6-one obtained in Reference Example 16, Compound 36 is obtained in a manner similar to Example 28.

EXAMPLE 37

2-Dicyclopropyl-5-n-butyl-3-methyl-3,4,5,7,8,9-hexahydropyrimido[2,1-b]purin-4-one (Compound 37)

Using 2-chloro-8-dicyclopropylmethyl-1-n-butyl-7-methyl-1,7-dihydro-6H-purin-6-one obtained in Reference Example 17, Compound 37 is obtained in a manner similar to Example 28.

EXAMPLE 38

2-Styryl-5-n-butyl-3-methyl-3,4,5,7,8,9-hexahydropyrimido[2,1-b]purin-4-one (Compound 38)

Using 2-chloro-8-styryl-1-n-butyl-7-methyl-1,7-dihydro-6H-purin-6-one obtained in Reference Example 18, Compound 38 is obtained in a manner similar to Example 28.

EXAMPLE 39

5-Methyl-2-(noradamantan-3-yl)-3,5,7,8-tetrahydro-4H-imidazo[2,1-b]purin-4-one (Compound 39)

Using 2-Benzylthio-1-methyl-8-(noradamantan-3-yl)-9-trityl-1,7-dihydro-6H-purin-6-one obtained in Reference Example 22, Compound 39 is obtained in a manner similar to Example 29.

EXAMPLE 40

2-Dicyclopropylmethyl-5-methyl-3,5,7,8-tetrahydro-4H-imidazo[2,1-b]purin-4-one (Compound 40)

Using 2-Benzylthio-8-dicyclopropylmethyl-1-methyl-9-trityl-1,7-dihydro-6H-purin-6-one obtained in Reference Example 23, Compound 40 is obtained in a manner similar to Example 29.

EXAMPLE 41

2-Styryl-5-methyl-3,5,7,8-tetrahydro-4H-imidazo[2,1-b]purin-4-one (Compound 41)

Using 2-benzylthio-1-methyl-8-styryl-9-trityl-1,7-dihydro-6H-purin-6-one obtained in Reference Example 24, Compound 41 is obtained in a manner similar to Example 29.

REFERENCE EXAMPLE 1

3,7-Dihydro-7-methyl-6-methylthio-3-n-propyl-2H-purin-2-one (Compound a)

Under an argon atmosphere, 10.7 g (268 mmol) of 60% sodium hydride was washed 3 times with n-hexane. The solvent was evaporated under reduced pressure to dry. To the residue was added 300 ml of dimethylformamide. A suspension of 3-n-propyl-6-thioxanthine (Japanese Published Unexamined Patent Application No. 183286/86) (28.2 g, 134 mmol) in 200 ml of dimethylformamide was dropwise added to the mixture under ice cooling with stirring. 15 minutes after, 25.1 ml (403 mmol) of methyl iodide was dropwise added to the reaction mixture. After stirring was continued for 30 minutes, 50 ml of ethanol was added and the mixture was concentrated. 250 ml of water was added to the residue and the precipitate was collected by filtration to give 25.9 g (yield, 81%) of Compound a.

Melting point: 224.7°-226.4° C. (acetonitrile).

Elemental analysis: as $C_{10}H_{14}N_4OS$ Found (%): C 50.30 H 5.95 N 23.35. Calcd. (%): C 50.40 H 5.92 N 23.51.

IR (KBr) $\nu$max (cm$^{-1}$) 1630, 1596, 1557, 1393.

$^1$H-NMR (CDCl$_3$) δ (ppm): 7.53(s, 1H), 4.16(t, 2H), 4.01(s, 3H), 2.71(s, 3H), 1.95–1.77(m, 2H), 0.98 (t, 3H).

$^{13}$H-NMR (CDCl$_3$) δ (ppm): 160.9, 154.7, 151.6, 143.3, 114.3, 45.0, 34.7, 21.2, 12.2, 11.2.

REFERENCE EXAMPLE 2

3,7-Dihydro-6-methylthio-3-n-propyl-2H-purin-2-one (Compound b)

Under an argon atmosphere, 9.77 g (244 mmol) of 60% sodium hydride was washed 3 times with n-hexane. The solvent was evaporated under reduced pressure to dry. To the residue was added 900 ml of dimethylformamide. Under ice cooling, 57.0 g (271 mmol) of 3-n-propyl-6-thioxanthine (Japanese Published Unexamined Patent Application No. 183287/86) was gently added to the mixture. 15 minutes after, 15.2 ml (244 mmol) of methyl iodide was dropwise added to the reaction solution. After stirring was continued for 30 minutes, 50 ml of ethanol was added and the mixture was concentrated under reduced pressure. After 400 ml of water was added to the residue, the precipitate was collected by filtration to afford 13.9 g (yield, 23%) of Compound b as a light yellow powder. The filtrate was extracted 5 times with 200 ml of chloroform. After washing with saturated sodium chloride aqueous solution, the filtrate was dried over anhydrous sodium sulfate and the solvent was evaporated under reduced pressure. The residue was isolated and purified by silica gel column chromatography (eluting solvent; 10% methanol/chloroform) to afford further 16.0 g (yield, 26%) of Compound b as a light yellow powder.

Melting point: 240.8°-242.5° C.

IR (KBr) $\nu$max (cm$^{-1}$) 3400(br), 1600, 1588, 1572.

$^1$H-NMR (DMSO-d δ (ppm): 13.54(brs, 1H), 8.13(brs, 1H), 3.99(t, 2H), 2.57(s, 3H), 1.80–1.62(m, 2H), 0.88(t, 3H).

$^{13}$C-NMR (DMSO-d$_6$) δ (ppm): 160.6(br), 153.8, 149.4(br), 141.9(br), 112.8(br), 44.4, 20.6, 11.3, 11.0.

MS (m/e): 224(M$^+$), 195, 182, 135.

REFERENCE EXAMPLE 3

8-Cyclopentyl-3-n-propylxanthine (Compound c)

To a suspension of 5,6-diamino-1-propyl-2,4(1H, 3H)pyrimidinedione (Japanese Published Unexamined Patent Application No. 57517/80) in 600 ml of dimethylformamide were sequentially added 17.7 ml (163 mmol) of cyclopentanecarboxylic acid, 30.0 g (196 mmol) of hydroxybenzotriazole and 50.5 g (245 mmol) of dicyclohexylcarbodiimide. The mixture was stirred at room temperature overnight. Insoluble materials were filtered off and the solvent was evaporated under reduced pressure After 600 ml of 4N aqueous sodium hydroxide solution was added to the residue, the mixture was refluxed for 10 minutes under heating. Under ice cooling, insoluble materials were filtered off and 50 ml of methanol was added to the filtrate. After neutralization with conc. hydrochloric acid, the precipitate was collected by filtration to afford 28.3 g (yield, 66%) of Compound c.

Melting point: 311.3°–313.1° C. (dimethylformamide).

Elemental analysis: as $C_{13}H_{18}N_4O_2$ Found (%): C 59.56 H 6.96 N 21.69. Calcd. (%): C 59.52 H 6.92 N 21.36.

IR (KBr) $\nu$max (cm$^{-1}$) 3150, 2880, 1698, 1669.

$^1$H-NMR (DMSO-$d_6$) $\delta$ (ppm): 13.05(brs, 1H), 10.94(s, 1H), 3.86(t, 2H), 3.18–3.04(m, 1H), 2.05–1.55(m, 10H), 0.87(t, 3H).

$^{13}$C-NMR (DMSO-$d_6$)) $\delta$ (ppm): 157.7, 154.3, 150.9, 149.4, 106.5, 43.3, 39.0, 31.9, 25.0, 20.9, 10.9.

REFERENCE EXAMPLE 4

8-Cyclopentyl-3-n-propyl-6-thioxanthine (Compound d)

A mixture of Compound c obtained in Reference Example 3 (14.1 g, 53.8 mmol) and phosphorous pentasulfide (19.5 g, 87.7 mmol) in 280 ml of pyridine was refluxed for 4 hours. The reaction mixture was poured into 600 ml of ice water and the precipitate was collected by filtration. The filtrate was concentrated under reduced pressure and the precipitate was collected by filtration again. The filtrate was combined and 400 ml of 2N aqueous sodium hydroxide solution was added to the crystals. After insoluble materials were removed, the system was neutralized with conc. hydrochloric acid and the precipitate was collected by filtration to afford Compound d as the crude product. The crude product was recrystallized from ethanol-water to afford 13.5 g (yield, 90%) of Compound d as light yellow plates.

Melting point: 214.3°–215.9° C.

Elemental analysis: as $C_{13}H_{18}N_4O \cdot \frac{1}{4}C_2H_5OH$ Found (%): C 56.17 H 6.76 N 19.44. Calcd. (%): C 55.93 H 6.78 N 19.33.

IR (KBr) $\nu$max (cm$^{-1}$): 2960, 1663, 1605, 1510, 1403.

$^1$H-NMR (DMSO-$d_6$) $\delta$ (ppm): 13.03(brs, 1H), 12.04(brs, 1H), 3.90(t, 2H), 3.30–3.10(m, 1H), 2.05–1.55(m, 10H), 0.87(t, 3H).

$^{13}$C-NMR (DMSO-$d_6$) $\delta$ (ppm): 173.3, 161.5, 148.9, 145.7, 118.5, 56.0, 43.8, 38.7, 32.0, 25.2, 20.7, 18.5, 10.9.

REFERENCE EXAMPLE 5

8-Cyclopentyl-3,7-dihydro-6-methylthio-3-n-propyl-2H-purin-2-one (Compound e)

Using 6.00 g (21.6 mmol) of Compound d obtained in Reference Example 4, the procedure was performed in a manner similar to Reference Example 2 to afford 4.70 g (yield, 75%) of Compound e as a light yellow powder.

Melting point: 257.5°–259.2° C.

Elemental analysis: as $C_{14}H_{20}N_4OS$ Found (%): C 57.77 H 7.22 N 19.36. Calcd. (%): C 57.51 H 6.89 N 19.16.

IR (KBr) $\nu$max (cm$^{-1}$): 1599, 1580, 1553, 1513

$^1$H-NMR (CDCl$_3$, 90 MHz) $\delta$ (ppm): 4.24(t, 2H), 3.53–3.15 (m, 1H), 2.10(s, 3H), 2.50–1.50(m, 10H), 0.95 (t, 3H).

REFERENCE EXAMPLE 6

8-Cyclopentyl-3,7-dihydro-7-methyl-6-methylthio-3-n-propyl-2H-purin-2-one (Compound f)

After 1.50 g (5.4 mmol) of Compound d obtained in Reference Example 4 was dissolved in 23 ml of dimethylformamide, 432 mg (10.8 mmol) of sodium hydride (60% oily) was gently added to the solution under ice cooling. The mixture was stirred for 30 minutes under ice cooling. The reaction mixture was poured into ice water and the precipitate was collected by filtration. After washing with water and then with 50% ether/hexane, 1.47 g (yield, 89%) of Compound f was obtained as a light yellow powder.

$^1$H-NMR (CDCl$_3$, 90 MHz) $\delta$ (ppm): 4.15(t, 2H), 3.91(s, 3H), 3.20–2.95(m, 1H), 2.68(s, 3H), 2.20–1.50(m, 10H), 0.90(t, 2H).

REFERENCE EXAMPLE 7

3-Benzyl-6-thioxanthine (Compound g)

Using 31.0 g (128 mmol) of 3-benzylxanthine [Biochemistry, 16, 3316 (1977)], the procedure was performed in a manner similar to Reference Example 4 to afford 28.7 g (yield, 87%) of Compound g as a light yellow powder.

Melting point: 261.8°–263.1° C. (DMSO-water).

IR (KBr) $\nu$max (cm$^{-1}$): 1682, 1600, 1560, 1426.

$^1$H-NMR (DMSO-$d_6$, 90 MHz) $\delta$ (ppm): 13.4(brs, 1H), 12.2 (brs, 1H), 7.99(s, 1H), 7.50–7.05(m, 5H), 5.12 (s, 2H).

REFERENCE EXAMPLE 8

3-Benzyl-3,7-dihydro-7-methyl-6-methylthio-2H-purin-2-one (Compound h) and
3-benzyl-3,7-dihydro-6-methylthio-2H-purin-2-one (Compound i)

Using 14 g (54.3 mmol) of Compound g obtained in Reference Example 7, the procedure was performed in a manner similar to Reference Example 2. The crude product was purified by silica gel column chromatography. The fraction was concentrated and eluted with 5% methanol/chloroform, to obtain 5.86 g (yield, 40%) of Compound h as a light yellow powder.

Melting point: 268.1°–269.8° C.

Elemental analysis: as $C_{13}H_{12}N_4OS$ Found (%): C 57.42 H 4.13 N 20.14. Calcd. (%) C 57.34 H 4.44 N 20.57.

IR (KBr) $\nu$max (cm$^{-1}$) 3420(br), 1600, 1566, 1543.

$^1$H-NMR (DMSO-$d_6$, 90 MHz) $\delta$ (ppm): 13.50(brs, 1H), 8.07 (s, 1H), 7.45–7.05(m, 5H), 5.22(s, 2H), 2.60(s, 3H).

MS (m/e):272(M+), 257, 225, 91, 65.

The fraction eluted with 2% methanol/chloroform in the silica gel column chromatography described above was concentrated. Using 7.24 g of the residue obtained, the procedure was performed in a manner similar to Reference Example 1 to afford 5.13 g (yield, 33%) of Compound i as a light yellow powder.

Melting point: 214.8°–216.4° C.

IR (KBr) νmax (cm$^{-1}$) 1633, 1591, 1558.

$^1$H-NMR (CDCl$_3$, 90 MHz) δ (ppm): 7.47(s, 1H), 7.60–7.05 (m, 5H), 5.32(s, 2H), 3.82(s, 3H), 2.67(s, 3H).

MS (m/e): 286(M+), 271, 228, 211, 195, 91.

REFERENCE EXAMPLE 9

1-n-Butyl-2-chloro-1,7-dihydro-7-methyl-6H-purin-6-one (Compound j)

To a suspension of 2-chloro-7-methyl-1,7-dihydro-6H-purin-6-one [Ber., 30, 2400 (1897)] (6.68 g, 0.0362 mol) was added 2.03 g (0.0507 mol) of 60% sodium hydride, and the mixture was stirred for 30 minutes. To the mixture was added 8.24 ml (0.0724 mol) of iodobutane. The mixture was stirred at an external temperature of 65° C. for further 30 minutes. The solvent was evaporated under reduced pressure and the obtained residue was purified by silica gel column chromatography (eluting solvent: chloroform:methanol=20:1) to afford 5.38 g (61.8%) of Compound j as light yellow crystals.

$^1$H-NMR (CDCl$_3$, 90 MHz) δ (ppm): 8.23(s, 1H), 4.59(t, 2H, J=7Hz), 4.06(s, 3H), 2.07–1.26(m, 4H), 1.03 (t, 3H, J=7Hz).

REFERENCE EXAMPLE 10

3,7-Dihydro-6-methylthio-8-(noradamantan-3-yl)-3-n-propyl-2H-purin-2-one (Compound k)

After 10 g of (30.3 mmol) of 8-(Noradamantan-3-yl)-3-n-propyl-6-thioxanthine was suspended in 90 ml of water, 30 ml of 2N aqueous sodium hydroxide solution and 60 ml of ethanol were added to the suspension. Under stirring, 2.83 ml (45.5 mmol) of methyliodide was dropwise added to the mixture. After stirring for 1 hour, the mixture was neutralized and extracted 3 times with chloroform. The extracts were combined, and dried over anhydrous sodium sulfate. The solvent was evaporated under reduced pressure to afford 9.81 g (yield, 94%) of Compound k as an amorphous powder.

$^1$H-NMR (CDCl$_3$, 90 MHz) δ (ppm): 13.3(brs, 1H), 4.23 (t, 2H), 2.80(t, 1H), 2.50–1.45(m, 14H), 1.95(s, 3H), 0.96(t, 3H).

REFERENCE EXAMPLE 11

8-Dicycropropylmethyl-3,7-dihydro-6-methylthio-3-n-propyl-2H-purin-2-one (Compound l)

Using 2.33 g (7.66 mmol) of 8-dicyclopropylmethyl-3-n-propyl-6-thioxanthine, the procedure was performed in a manner similar to Reference Example 10 to afford 2.76 g (quantitative) of Compound l as a light yellow powder.

$^1$H-NMR (CDCl$_3$, 90 MHz) δ (ppm): 4.23(t, 2H), 2.10–0.10 (m, 13H), 1.93(s, 3H), 0.93(t, 3H).

REFERENCE EXAMPLE 12

3-n-Propyl-8-styryl-6-thioxanthine (Compound m)

After 4.14 g (14.0 mmol) of 3-n-propyl-8-styrylxanthine was suspended in 80 ml of pyridine, 5.07 g (22.8 mmol) of phosphoruspentasulfide was added to the suspension, and the mixture was refluxed for 2.5 hours under heating. After the mixture was poured into 300 ml of an ice water, a precipitate was collected by filtration, and suspended in 150 ml of 2N sodium hydroxide. The suspension was stirred for 30 minutes at room temperature and insoluble matters were removed by filtration. A filtrate was neutralized, and a precipitated was collected by filtration to afford 4.25 g (yield, 97%) of Compound m as a yellow powder.

Melting point: >290° C. (dioxane-water).

Elemental analysis: as C$_{16}$H$_{16}$N$_4$OS.$\frac{1}{2}$C$_4$H$_8$O$_2$ Found (%): C 60.60 H 5.65 N 15.73. Calcd. (%): C 60.65 H 5.65 N 15.72.

IR (KBr) νmax (cm$^{-1}$) 1689, 1604, 1511.

$^1$H-NMR (DMSO-d$_6$, 90 MHz) δ (ppm): 7.85(d, J=16.0Hz, 1H), 7.70–7.35(m, 5H), 7.20(d, J=16.0Hz, 1H), 3.99(t, 2H), 2.00–1.65(m, 2H), 0.93(t, 3H).

MS (m/e, relative intensity): 312(M+, 100), 269(35), 252(18).

REFERENCE EXAMPLE 13

3,7-Dihydro-7-methyl-6-methylthio-3-n-propyl-8-styryl-2H-purin-2-one (Compound n)

Using 2.00 g (6.41 mmol) of Compound m obtained in Reference Example 12, the procedure was performed in a manner similar to Reference Example 1 to afford 1.73 g (yield, 79%) of Compound n as a light yellow powder.

$^1$H-NMR (CDCl$_3$, 90 MHz) δ (ppm): 7.91(d, J=15.5Hz, 1H), 7.70–7.35(m, 5H), 6.92(d, J=15.5Hz, 1H), 4.20 (t, 2H), 4.04(s, 3H), 2.70(s, 3H), 2.10–1.70(m, 2H), 1.02(t, 3H).

REFERENCE EXAMPLE 14

2-Benzylthio-9-trityl-1,7-dihydro-6H-purin-6-one (Compound o)

2.00 g (11.9 mmol) of 2-mercapto-6-hydroxypurine was dissolved in a solvent mixture of 10 ml of ethanol, 10.9 ml of 2N sodium hydroxide and 15 ml of water. Under ice cooling with stirring, 2.06 ml (17.9 mmol) of benzylbromide was added to the solution, following stirring at room temperature for 30 minutes. Again under ice cooling, the mixture was neutralized with 2N hydrochloric acid and 30 ml of n-hexane was added to the mixture. A precipitated was collected by filtration, washed with ethyl acetate and dried to afford 1.32 g (yield, 45%) of 2-benzylthio-6-hydroxypurine as a crude product.

1.00 g (3.88 mmol) of 2-benzylthio-6-hydroxypurine was dissolved in 20 ml of dimethylformamide and 0.816 ml (5.82 mmol) of triethylamine was added to the solution. Under ice cooling, 1.62 g (5.82 mmol) of tritylchloride was added to the mixture following stirring at room temperature overnight. After 400 ml of water was added, a precipitate was collected by filtration and washed with n-hexane and with ethyl acetate. Recrystallization from ethanol afforded 0.785 g (yield, 40%) of Compound o as a white powder.

Melting point: 267°–270° C.

Elemental analysis: as C$_{31}$H$_{24}$N$_4$OS Found (%): C 74.33 H 4.87 N 11.30. Calcd. (%): C 74.38 H 4.83 N 11.19.

IR (KBr) νmax (cm$^{-1}$): 1683, 1554.

$^1$H-NMR (CDCl$_3$, 90 MHz) δ (ppm): 7.76(s, 1H), 6.75–7.61 (m, 20H), 4.38(s, 2H).

MS (m/e): 260(M+-C$_6$H$_5$X$_3$+1).

REFERENCE EXAMPLE 15

2-Benzylthio-1-methyl-9-trityl-1,7-dihydro-6H-purin-6-one (Compound p)

After 500 mg (0.10 mmol) of Compound o obtained in Reference Example 14 was dissolved in 20 ml of tetrahydrofuran, 0.08 g (0.20 mmol) of 60% sodium hydroxide was added to the solution under ice cooling. After 30 minutes, 0.125 ml (0.20 mmol) of methyliodide was added, and the mixture was stirred for 2 hours at 50° C. The solvent was evaporated under reduced pressure, and water was added to the residue. The mixture was extracted with chloroform, and the extract was washed with a saturated aqueous sodium chloride, dried over anhydrous sodium sulfate and filtered. The solvent was evaporated under reduced pressure, and the residue was purified by silicagelcolumchromatography (eluent: chloroform) to afford 300 mg (yield, 58%) of Compound p as a white powder.

Melting point: 255°–258° C. (isopropanol-water).

Elemental analysis: as $C_{32}H_{26}N_4OS$ Found (%): C 75.00 H 5.11 N 10.96. Calcd. (%): C 74.68 H 5.09 N 10.89.

IR (KBr) $\nu$max (cm$^{-1}$): 1700, 1555.

$^1$H-NMR (CDCl$_3$) $\delta$ (ppm): 7.64(s, 1H), 7.07–7.46(m, 18H), 6.94–6.98(m, 2H), 3.49(s, 3H), 3.48(s, 2H).

REFERENCE EXAMPLE 16

2-Chloro-8-(noradamantan-3-yl)-1-n-butyl-7-methyl-1,7-dihydro-6H-purin-6-one

The procedure is performed in a manner similar to Reference Example 9 except for using 2-chloro-8-(noradamantan-3-yl)-7-methyl-1,7-dihydro-6H-purin-6-one to afford the captioned compound.

REFERENCE EXAMPLE 17

2-Chloro-8-dicyclopropylmethyl-1-n-butyl-7-methyl-1,7-dihydro-6H-purin-6-one

The procedure is performed in a manner similar to Reference Example 9 except for using 2-chloro-8-dicyclopropylmethyl-7-methyl-1,7-dihydro-6H-purin-6-one to afford the captioned compound.

REFERENCE EXAMPLE 18

2-Chloro-8-styryl-1-n-butyl-7-methyl-1,7-dihydro-6H-purin-6-one

The procedure is performed in a manner similar to Reference Example 9 except for using 2-chloro-8-styryl-7-methyl-1,7-dihydro-6H-purin-6-one to afford the captioned compound.

REFERENCE EXAMPLE 19

2-Benzylthio-8-(noradamantan-3-yl)-9-trityl-1,7-dihydro-6H-purin-6-one

The procedure is performed in a manner similar to Reference Example 14 except for using 8-(noradamantan-3-yl)-2-mercapto-6-hydroxypurin to afford the captioned compound.

REFERENCE EXAMPLE 20

2-Benzylthio-8-dicyclopropylmethyl-9-trityl-1,7-dihydro-6H-purin-6-one

The procedure is performed in a manner similar to Reference Example 14 except for using 8-dicyclopropylmethyl-2-mercapto-6-hydroxypurin to afford the captioned compound.

REFERENCE EXAMPLE 21

2-Benzylthio-8-styryl-9-trityl-1,7-dihydro-6H-purin-6-one

The procedure is performed in a manner similar to Reference Example 14 except for using 8-styryl-2-mercapto-6-hydroxypurin to afford the captioned compound.

REFERENCE EXAMPLE 22

2-Benzylthio-1-methyl-8-(noradamantan-3-yl)-9-trityl-1,7-dihydro-6H-purin-6-one

The procedure is performed in a manner similar to Reference Example 15 using the compound obtained in Reference Example 19 to afford the captioned compound.

REFERENCE EXAMPLE 23

2-Benzylthio-8-dicyclopropylmethyl-1-methyl-9-trityl-1,7-dihydro-6H-purin-6-one

The procedure is performed in a manner similar to Reference Example 15 using the compound obtained in Reference Example 20 to afford the captioned compound.

REFERENCE EXAMPLE 24

2-Benzylthio-1-methyl-8-styryl-9-trityl-1,7-dihydro-6H-purin-6-one

The procedure is performed in a manner similar to Reference Example 15 using the compound obtained in Reference Example 21 to afford the captioned compound.

PREPARATION EXAMPLE 1

Tablet

Tablet comprising the following composition is prepared in a conventional manner.

| | |
|---|---|
| Compound 6 | 20 mg |
| Lactose | 60 mg |
| Potato starch | 30 mg |
| Polyvinyl alcohol | 3 mg |
| Magnesium stearate | 1 mg |

PREPARATION EXAMPLE 2

Powder

Powder comprising the following composition is prepared in a conventional manner.

| | |
|---|---|
| Compound 1 | 20 mg |
| Lactose | 300 mg |

PREPARATION EXAMPLE 3

Syrup

Syrup comprising the following composition is prepared in a conventional manner.

| | |
|---|---|
| Compound 7 | 20 mg |
| Refined white sugar | 30 mg |
| Ethyl p-hydroxybenzoate | 40 mg |
| Propyl p-hydroxybenzoate | 10 mg |
| Strawberry flavor | 0.1 cc |
| Water to make the whole volume | 100 cc. |

PREPARATION EXAMPLE 4

Capsule

Capsule comprising the following composition is prepared in a conventional manner.

| Compound 6 | 20 mg |
|---|---|
| Lactose | 200 mg |
| Magnesium stearate | 5 mg |

The above components are mixed and the mixture is filled up in a gelatin capsule.

PREPARATION EXAMPLE 5

Injection

| Compound 7 | 20 mg |
|---|---|
| Sodium chloride | 45 mg |

Sterilized water for injection is added to the above components to make the whole volume 5 ml (volume per ampoule). The solution is filtered and sterilized in an autoclave.

What is claimed is:

1. A condensed purin derivative represented by Formula (I):

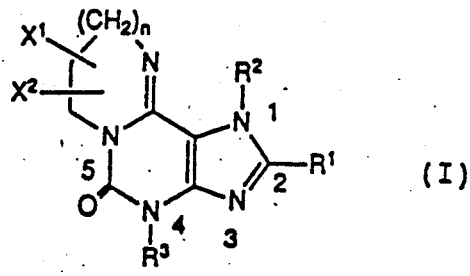

wherein:
$R^1$ represents cycloalkyl having 3 to 6 carbon atoms, noradamantan-3-yl, dicyclopropylmethyl or styryl;
$R^2$ represents hydrogen, lower alkyl or cycloalkyl having 3 to 6 carbon atoms;
$R^3$ is lower alkyl;
n is an integer of 0 or 1, and each of $X^1$ and $X^2$ independently represents hydrogen, lower alkyl, aralkyl or phenyl; or a pharmaceutically acceptable salt thereof.

2. The compound according to claim 1, wherein n is 0.

3. The compound according to claim 1, wherein the cycloalkyl having 3 to 6 carbon atoms being cyclopropyl, cyclopentyl or cyclohexyl.

4. The compound according to claim 3, wherein $X^1$ is hydrogen.

5. The compound according to claim 3, wherein $X^1$ is ethyl and $X^2$ is hydrogen.

6. A compound which is selected from the group consisting of: 2-cyclopentyl-8-ethyl-4-n-propyl-1,4,7,8-tetrahydro-5H-imidazo[2,1-i]purin-5-one; 8-ethyl-2-(noradamantan-3-yl)-4-n-propyl-1,4,7,8-tetrahydro-5H-imidazo[2,1-i] purin-5-one; 2-(dicyclopropylmethyl)-8-ethyl-4-n-propyl-1,4,7,8-tetrahydro-5H-imidazo[2,1-i] purin-5-one; 8-ethyl-1-methyl-4-n-propyl-2-styryl-1,4,7,8-tetrahydro-5H-imidazo[2,1-i] purin-5-one and a pharmaceutically acceptable salt thereof.

7. A compound according to claim 6 or 1, wherein said salt is selected from the group consisting of a pharmaceutically acceptable acid addition salt, a pharmaceutically acceptable metal salt, a pharmaceutically acceptable ammonium salt, a pharmaceutically acceptable organic amine addition salt and a pharmaceutically acceptable amino acid addition salt.

8. A pharmaceutical composition comprising a pharmaceutical carrier and as an active ingredient, an effective amount of the compound as defined by claim 6 or 1.

* * * * *

UNITED STATES PATENT AND TRADEMARK OFFICE
CERTIFICATE OF CORRECTION

PATENT NO. : 5,270,316
DATED : December 14, 1993
INVENTOR(S) : FUMIO SUZUKI, ET AL.

It is certified that error appears in the above-identified patent and that said Letters Patent is hereby corrected as shown below:

ON TITLE PAGE

In [57] ABSTRACT, line 2:
"formula;" should read --formula:--.

COLUMN 2

Line 50, salts, should read --salt,--.

COLUMN 3

Line 62, "80°C" should read --180°C.--.

COLUMN 8

TABLE I-1, under Compound No. 8, Col. $X^2$, insert: --"--.

COLUMN 13

Line 51, "induce" should read --induces--.

COLUMN 16

Line 53, "compound" should read --compounds--.

COLUMN 18

Line 2, "powder" should read --powder.--.

COLUMN 21

Line 15, "($cm^{-1}$)" should read --($cm^{-1}$):--.

UNITED STATES PATENT AND TRADEMARK OFFICE
CERTIFICATE OF CORRECTION

PATENT NO. : 5,270,316

DATED : December 14, 1993

INVENTOR(S) : FUMIO SUZUKI, ET AL.

Page 2 of 3

It is certified that error appears in the above-identified patent and that said Letters Patent is hereby corrected as shown below:

COLUMN 22

TABLE 8, under Compound No. 12:
" N          should read      -- N
16.82 "                          16.83 --.

COLUMN 30

Line 62, "(DMSO-d" should read --(DMSO-$d_6$)--.

COLUMN 31

Line 13, "pressure" should read --pressure.--.
Line 26, "($cm^{-1}$)" should read --($cm^{-1}$):--.
Line 30, "(DMSO-$d_6$))" should read --(DMSO-$d_6$)--.

COLUMN 32

Line 60, "($cm^{-1}$)" should read --($cm^{-1}$):--.

COLUMN 33

Line 4, "($cm^{-1}$)" should read --($cm^{-1}$):--.

COLUMN 34

Line 7, "($cm^{-1}$)" should read --($cm^{-1}$):--.
Line 39, "precipitated" should read --precipitate--.

UNITED STATES PATENT AND TRADEMARK OFFICE
CERTIFICATE OF CORRECTION

PATENT NO. : 5,270,316

DATED : December 14, 1993

INVENTOR(S) : FUMIO SUZUKI, ET AL.

It is certified that error appears in the above-identified patent and that said Letters Patent is hereby corrected as shown below:

COLUMN 35

Line 10, "silicagelcolumchromatography" should read --silica gel column chromatography--.

COLUMN 37

Line 48, "purin" should read --purine--.

COLUMN 38

Line 25, "being" should read --is--.
Line 38, "and" should read --or--.

Signed and Sealed this

Thirtieth Day of August, 1994

Attest:

BRUCE LEHMAN

Attesting Officer

Commissioner of Patents and Trademarks